US006713488B2

(12) United States Patent
Sadée et al.

(10) Patent No.: US 6,713,488 B2
(45) Date of Patent: Mar. 30, 2004

(54) NEUTRAL ANTAGONISTS AND USE THEREOF IN TREATING DRUG ABUSE

(76) Inventors: Wolfgang Sadée, P.O. Box 232, Ross, CA (US) 94957; Danxin Wang, 1234 6th Ave., Apt. #3, San Francisco, CA (US) 94122

(*) Notice: Subject to any disclaimer, the term of this patent is extended or adjusted under 35 U.S.C. 154(b) by 0 days.

(21) Appl. No.: 10/173,337

(22) Filed: Jun. 14, 2002

(65) Prior Publication Data

US 2003/0069262 A1 Apr. 10, 2003

Related U.S. Application Data

(63) Continuation of application No. 09/809,637, filed on Mar. 15, 2001, now abandoned.
(60) Provisional application No. 60/189,372, filed on Mar. 15, 2000.

(51) Int. Cl.[7] ............................................. A61K 31/485
(52) U.S. Cl. ........................................................ 514/282
(58) Field of Search ................................. 514/282

(56) References Cited

U.S. PATENT DOCUMENTS

| | | | |
|---|---|---|---|
| 3,254,088 A | 5/1966 | Lewenstein et al. | 260/285 |
| 3,332,950 A | 7/1967 | Blumberg et al. | 260/285 |
| 3,523,906 A | 8/1970 | Vrancken et al. | 252/316 |
| 3,691,090 A | 9/1972 | Kitajima et al. | 252/316 |
| 3,737,337 A | 6/1973 | Schnoring et al. | 117/100 |
| 3,891,570 A | 6/1975 | Fukushima et al. | 252/316 |
| 3,960,757 A | 6/1976 | Morishita et al. | 252/316 |
| 4,389,330 A | 6/1983 | Tice et al. | 427/213.36 |
| 4,689,332 A | 8/1987 | McLaughlin et al. | 514/282 |
| 4,760,069 A | 7/1988 | Rzeszotarski et al. | 514/282 |

(List continued on next page.)

FOREIGN PATENT DOCUMENTS

| | | | |
|---|---|---|---|
| CH | 683005 A5 | 12/1993 | |
| WO | WO 96/14071 | 5/1996 | |
| WO | WO 98/52565 | 11/1998 | |

OTHER PUBLICATIONS

Fujimoto, J.M., et al., "Narcotic Antagonist Activity of Several Metabolites of Naloxone and Naltrexone Tested in Morphine Dependent Mice," *Proceedings of the Society for Experimental Biology and Medicine,* 148:443–448 (1975).
Wang, Z., et al., "Constitutive μ Opioid Receptor Activation as a Regulatory Mechanism Underlying Narcotic Tolerance and Dependence," *Life Sciences,* 54(20):PL339–350 (1994).
Bilsky, E.J., et al., "Effects of Naloxone and D–Phe–Cys–Tyr–D–Trp–Arg–Thr–Pen–Thr–$NH_2$ and the Protein Kinase Inhibitors H7 and H8 on Acute Morphine Dependence and Antinociceptive Tolerance in Mice," *The Journal of Pharmacology and Experimental Therapeutics,* 277(1):484–490 (1996).

(List continued on next page.)

*Primary Examiner*—James H Reamer
(74) *Attorney, Agent, or Firm*—Mueller and Smith, LPA

(57) ABSTRACT

The invention relates to the use of naltrexone and naloxone analogs, which are neutral antagonists at the μ opioid receptor, for the treatment of drug dependency in a drug-dependent individual. Surprisingly, it has been found that administration of a therapeutically effect amount of the naloxone or naltrexone analogs described herein for the treatment of a drug dependency, can result in reduction of undesirable side effects resulting from current treatments using naloxone and naltrexone. For example, the treatment described herein can result in a reduction in the withdrawal symptoms and aversion encountered in the use of naloxone and naltrexone in the treatment of drug dependency. In addition, the naltrexone and naloxone analogs of the invention can be used for the treatment of pain in an individual in need thereof by modulating opoid pain treatment using neutral antagonists, for example, reversing respiratory depression withough causing other adverse effects. In addition, during chronic use of opioid drugs for pain therapy, neutral antagonists can be used to diminish constipation peripherally without effecting the central analgesic effects.

29 Claims, 7 Drawing Sheets

U.S. PATENT DOCUMENTS

| | | | |
|---|---|---|---|
| 4,816,586 A | 3/1989 | Portoghese | 544/340 |
| 4,889,860 A | 12/1989 | Rzeszotarski et al. | 514/282 |
| 5,019,400 A | 5/1991 | Gombotz et al. | 424/497 |
| 5,051,426 A | 9/1991 | Parnell | 514/263 |
| 5,256,669 A | 10/1993 | Askanazi et al. | 514/282 |
| 5,266,574 A | 11/1993 | Zagon et al. | 514/282 |
| 5,426,112 A | 6/1995 | Zagon et al. | 514/282 |
| 5,650,173 A | 7/1997 | Ramstack et al. | 424/489 |
| 5,656,297 A | 8/1997 | Bernstein et al. | 424/484 |
| 5,681,830 A | 10/1997 | Chang et al. | 514/85 |
| 5,760,044 A | 6/1998 | Archer | 514/282 |
| 5,780,479 A * | 7/1998 | Kim | 514/282 |
| 5,792,477 A | 8/1998 | Rickey et al. | 424/501 |
| 5,852,032 A * | 12/1998 | Mason | 514/282 |
| 5,854,249 A | 12/1998 | Chang et al. | 514/255 |
| 5,882,944 A | 3/1999 | Sadee | 436/501 |
| 5,916,598 A | 6/1999 | Rickey et al. | 424/501 |
| 5,922,253 A | 7/1999 | Herbert et al. | 264/5 |
| 6,004,970 A | 12/1999 | O'Malley et al. | 514/282 |
| 6,007,986 A | 12/1999 | Sadee | 435/6 |
| RE36,547 E | 2/2000 | Crain et al. | 514/282 |
| 6,054,127 A | 4/2000 | Swain et al. | 424/194.1 |
| 6,109,269 A | 8/2000 | Rise et al. | 514/282 |
| 6,110,503 A | 8/2000 | Rickey et al. | 424/501 |
| 6,194,006 B1 | 2/2001 | Lyons et al. | 424/489 |

OTHER PUBLICATIONS

Ferrari, A., et al., "Serum Time Course of Naltrexone and 6β–Naltrexol Levels During Long Term Treatment in Drug Addicts," *Drug and Alcohol Dependence*, 52:211–220 (1998).

Gardner, E.L., "Brain Reward Mechanisms". In *Substance Abuse. A Comprehensive Textbook*, Fisher, M.G., eds., (MD:Williams & Wilkins), pp. 70–99 (1992).

Nestler, E. J., "Molecular Mechanisms of Drug Addiction," *The Journal of Neuroscience*, 12(7):2439–2450 (1992).

Chatterjie, N., and Inturrisi, C.E., "Stereospecific Synthesis of the 6β–Hydroxy Metabolites of Naltrexone and Naloxone," *Journal of Medicinal Chemistry*, 18(5):490–492 (1975).

Jiang, J.B., et al., "Stereochemical Studies on Medicinal Agents. 23.[1] Synthesis and Biological Evaluation of 6–Amino Derivatives of Naloxone and Naltrexone," *Journal of Medicinal Chemistry*, 20(8):1100–1102 (1977).

Burford, N.T., et al., "Specific G Protein Activation and μ–opioid Recepter Internalization Caused by Morphine, DAMGO and Endomorphin I," *European Journal of Pharmacology*, 342:123–126 (1998).

Wang, Danxin, et al., "Calmodulin Binding to G Protein–coupling Domain of Opioid Receptors," *The Journal of Biological Chemistry*, 274(31):22081–22088 (1999).

Burford, N.T., et al., "G–Protein Coupling of μ–Opioid Receptors ($OP_3$) : Elevated Basal Signalling Activity," *Biochemical Journal*, 348:531–537 (2000).

Wang, Danxin, et al., "Calmodulin Regulation of Basal and Agonist–Stimulated G Protein Coupling by the μ–Opioid Receptor ($OP_3$) in Morphine–Pretreated Cells," *Journal of Neurochemistry*, 75(2):763–771 (2000).

Comer, S.D., et al., "Clocinnamox: A Novel, Systemically–Active, Irreversible Opioid Antagonist[1,2,3]", *The Journal of Pharmacology and Experimental Therapeutics*, 262(3):1051–1056 (1992).

Palmer, R. B., et al., "(E) –and (Z)–7–Arylidenenaltrexones: Synthesis and Opioid Receptor Radioligand Displacement Assays," *J. Med. Chem.*, 40(5):749–753 (1997).

Neilan, C.L., et al., "Constitutive Activity of the δ–Opioid Receptor Expressed in C6 Glioma Cells: Identification of Non–Peptide δ–Inverse Agonists," *British Journal of Pharmacology*, 128(3):556–562 (1999).

Wong, Y.H., "$G_i$ Assays in Transfected Cells," *Methods in Enzymology*, 238:81–94 (1994).

Porreca, F., et al., "Roles of *Mu, Delta* and *Kappa* Opioid Receptors in Spinal and Supraspinal Mediation of Gastrointestinal Transit Effects and Hot–Plate Analgesia in the Mouse", *The Journal of Pharmacology and Experimental Therapeutics*, 230(2):341–348 (1984).

Plapp, B.V., "Control of Alcohol Metabolism". In *Toward a Molecular Basis of Alcohol Use and Abuse*, B. Jansson, et al., ed., (Birkhäuser Verlag Basel/Switzerland), pp. 311–322 (1994).

Yano, I., and Takemori, A.E., "Inhibition by Naloxone of Tolerance and Dependence in Mice Treated Acutely and Chronically with Morphine," *Research Communications in Chemical Pathology and Pharmacology*, 16(4):721–734 (1977).

Abstract for Accession No. 1993–406332/199351 from World Patent Index Database compiled by Derwent Information Limited.

* cited by examiner

NEUTRAL ANTAGONISTS AND USE THEREOF IN TREATING DRUG ABUSE

RELATED APPLICATION

This application is a continuation of U.S. application Ser. No. 09/809,637, filed on Mar. 15, 2001, now abandoned which claims the benefit of U.S. Provisional Application No. 60/189,372 filed on Mar. 15, 2000. The entire teachings of the above applications are incorporated herein by reference.

GOVERNMENT SUPPORT

The invention is made with government support under Grant Number DA04166, awarded by the National Institutes of Health. The government has certain rights in the invention.

BACKGROUND OF THE INVENTION

Endogenous opiate receptors were discovered in the 1970s, and have been intensely studied in seeking the mechanisms by which particular drugs lead to addiction. However, such mechanisms have remained elusive. See, for example, *J. Neurosci.*, 12(7): 2349–2450 (1992).

A number of different opioid receptor types have been identified. Known receptor types include, for example, the mu $\mu$ (MOR), delta $\delta$ (DOR), and $\kappa$ kappa receptors. Narcotic analgesics act at the opioid $\mu$ receptor to produce analgesia. The $\mu$ receptor mediates analgesia, respiratory depression, and inhibition of gastrointestinal transit. As such, narcotic analgesics act at the $\mu$ receptor to produce analgesia. However, continued use of narcotic analgesics typically leads to habit or addiction, and use of one leads to cross-tolerance/dependence for the others. Despite their therapeutic uses, undesirable side effects such as physical dependence and drug craving can develop.

Opiates, are a class of centrally acting compounds and are frequently used agents for pain control. Opiates are narcotic agonistic analgesics and are drugs derived from opium, such as morphine, codeine, and many synthetic congeners of morphine, with morphine being the most widely used derivative. Opioids are natural; and synthetic drugs with morphine-like actions and include the opiates. Opioids are narcotic agonistic analgesics which produce drug dependence of the morphine type and are subject to control under federal narcotics law because of their addicting properties. The chemical classes of opioids with morphine-like activity are the purified alkaloids of opium consisting of phenanthrenes and benzylisoquinolines, semi-synthetic derivatives of morphine, phenylpiperidine derivatives, morphinan derivatives, benzomorphan derivatives, diphenyl-heptane derivatives, and propionanilide derivatives.

Physical dependence or drug addiction to narcotic drugs, for example, opioids, has been traditionally treated by drug withdrawal through administering an opioid antagonistic drug such as naltrexone or naloxone, withholding the opioid from the drug-dependent individual, gradually decreasing the amount of opioid taken by the individual over time, or substituting another drug, such as methadone, buprenorphine, or methadyl acetate, for the opioid to ameliorate the physical need for the opioid. When an opioid is discontinued, withdrawal symptoms appear, the character and severity of which are dependent upon such factors as the particular opioid being withdrawn, the daily dose of the opioid that is being withdrawn, the duration of use of the opioid, and the health of the drug dependent individual. The pain associated with withdrawal symptoms can be quite severe.

For example, the withdrawal of morphine, heroin, or other opioid agonists with similar durations of action from an individual dependent upon the opioid gives rise to lacrimation, rhinorrhea, yawning, and sweating 8 to 12 hours after the last dose of the opioid. As withdrawal progresses, the individual will be subject to dilated pupils, anorexia, gooseflesh, restlessness, irritability, and tremor. At the peak intensity of withdrawal, which is 48 to 72 hours for morphine and heroin, the individual suffers from increasing irritability, insomnia, marked anorexia, violent yawning, severe sneezing, lacrimation, coryza, weakness, depression, increased blood pressure and heart rate, nausea, vomiting, intestinal spasm, and diarrhea. The individual commonly experiences chills alternating with hot flushes and sweating, as well as abdominal cramps, muscle spasms and kicking movements, and pains in the bones and muscles of the back and extremities, and exhibits leukocytosis and an exaggerated respiratory response to carbon dioxide. Typically the individual does not eat or drink which, when combined with the vomiting, sweating, and diarrhea, results in weight loss, dehydration, and ketosis. The withdrawal symptoms from morphine and heroin usually disappear in 7 to 10 days, but the drug dependent individual suffers greatly during the withdrawal period.

Alternatively, if an opioid antagonistic drug is administered to the individual, such as naloxone or naltrexone, withdrawal symptoms develop within a few minutes after parenteral administration and reach peak intensity within 30 minutes, with a more severe withdrawal than from withholding the opioid. For example, naloxone is the current treatment of choice in cases of overdose. It is immediately effective but is encumbered by intense withdrawal syndrome. Naltrexone can be used, for example, in maintenance therapy, but is quite aversive, which impedes wide acceptance and efficacy. Since addiction to cocaine and alcohol have been reported to also be mediated by specific opioid-sensitive brain cell networks (See, Gardner et al., *Substance Abuse* $2^{nd}$ *Ed.*, pp. 70–99 (1992)) the use of opioid antagonists can be suitable for use in the treatment of alcohol and cocaine dependency. Thus, the opioid receptors can play a role in the dependency of multiple drug substances.

The use of opioid analgesics for the treatment of pain and during and/or after anesthesia can also lead to unwanted side effects, for example, respiratory depression. It is frequently necessary to titrate back or adjust the degree of analgesic/anesthesia in an individual receiving opioid pain management, for example, undergoing or recovering from a surgical procedure, due to complications associated with too high of a dose. The use of naltrexone and naloxone present undesirable side effects such as exacerbation respiratory depression when used to titrate back. Further, use of opioid analgesics for chronic pain can often be associated with constipation which can be a significant and limiting problem. There is currently no known treatment strategy to reduce the constipating effects of the opioid analgesics without blocking the analgesic effect and/or causing additional side effects (e.g., diarrhea and hyperalgesia).

Therefore, a need exists for agents which can be used in the treatment of drug dependency or in pain management to, for example, modify the anesthesia/analgesia of an opioid drug or its unwanted side effects but which have reduced aversive properties and can result in reduced withdrawal symptoms.

SUMMARY OF THE INVENTION

The invention relates to the use of naltrexone and naloxone analogs, which are neutral antagonists at the $\mu$ opioid receptor, for the treatment of drug dependency in a drug-dependent individual. Surprisingly, it has been found that administration of a therapeutically effective amount of the naloxone or naltrexone analogs described herein for the treatment of a drug dependency, can result in reduction of undesirable side effects resulting from current treatments using naloxone and naltrexone. For example, the treatment described herein can result in a reduction in the withdrawal symptoms and aversion encountered in the use of naloxone and naltrexone in the treatment of drug dependency. In addition, the naltrexone and naloxone analogs of the invention can be used for modulating the treatment of pain or anesthesia in an individual in need thereof by decreasing or reversing the effects of high doses of the narcotic analgesic, for example, respiratory depression, or decreasing side effects such as constipation without blocking analgesia.

U.S. Pat. No. 6,007,986, teaches that the $\mu$ opioid receptor has a constitutively active state that may be represented as $\mu^*$. The $\mu$ opioid receptor is the main mediator of narcotic analgesia and addiction and can be classified as a G protein coupled receptor (GPCR). This feature of basal level signalling activity is emerging as a recognized feature of a number of GPCRs, for example, the dopamine receptors, D1, D2 and D3, the adenosine receptor, the $\beta$2-adrenergic receptor, the serotonin receptor (5HT-2A) and the $\delta$-opioid receptors. In the naive state (no prior drug exposure), the activity of the $\mu^*$ state is minimal, and most receptors are drug sensitive. Recent findings, indicate that the $\mu$ opioid receptor differs in its characteristics significantly between drug-naive and drug-tolerant/dependent states, with the constitutive or spontaneous activity of the $\mu$ opioid receptor being enhanced in the tolerant/dependent state.

In general, compounds which exhibit antagonistic behavior at a particular GPCR having basal signalling activity, for example the $\mu$ opioid receptor, can be categorized as either neutral antagonists or inverse agonists based on the effect which they exhibit upon the basal signalling activity of the particular receptor for which they are a ligand following interaction. "Neutral antagonists" are agents which block the affects of an agonist at the target receptor but do not significantly effect the level of spontaneous receptor activity. "Inverse agonists" are agents which block the effects of an agonist at the target receptor and also suppress spontaneous receptor activity.

Individual opioid drugs fall on a sliding scale of efficacy from full agonist to full inverse agonists. It appears possible that these pharmacological properties of a drug can change, however, during long-term stimulation. For example, it has been determined that the prototypical opioid antagonists naloxone and naltrexone, which display neutral antagonistic behavior at an untreated $\mu$ opioid receptor, behave as inverse agonist at drug-pretreated, for example, morphine pretreated receptors. This switch in pharmacological effects at untreated or drug-pretreated receptors can be at least in part responsible for the severe withdrawal symptoms experienced by drug-dependent individual upon administration of naloxone and naltrexone. Thus, withdrawal symptoms can be a result of not only the blocking of agonist effects, but the inverse agonist effect of naloxone and naltrexone on the spontaneously active $\mu$ opioid receptor.

Neutral antagonists against receptors exhibiting spontaneous activity can be determined with the use of in vitro assays described by U.S. Pat. No. 5,882,944, issued Mar. 16, 1999, and U.S. Pat. No. 6,007,986, issued Dec. 28, 1999, to Sadée and pending application Ser. No. 09/200,012 now U.S. Pat. No. 6,270,979 the entire contents of all of which are hereby incorporated by reference. For example, the peptide CTAP was identified as a neutral antagonist in these assays, and was shown to elicit significantly less withdrawal than naloxone in drug-dependent mice (*J. Pharm. Exper. Ther.*, 277: 484–190 (1996)).

Accordingly, the present invention relates to a method for the treatment of drug-dependency in a drug-dependent individual in need thereof comprising administering to the individual a therapeutically effect amount of a naloxone or naltrexone analog or a pharmaceutically acceptable salt thereof which is a neutral antagonist at the $\mu$ opioid receptor.

The naltrexone analogs suitable for use in the invention can be represented by Formula I and include the pharmaceutically acceptable salts thereof:

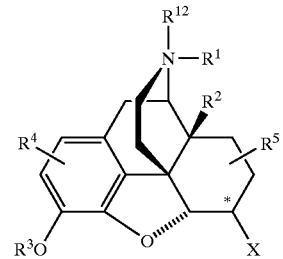

wherein:
  $R^1$ is cycloalkyl(alkyl), for example, $C_3$–$C_6$ (cycloalkyl) alkyl, for example, $C_3$–$C_6$(cycloalkyl)methyl such as (cyclopropy)lmethyl or $C_5$–$C_7$(cycloalkenyl)alkyl;
  $R^2$ is H, OH or esters thereof, such as —OAc($O_2$C (alkyl)), for example $O_2$($C_1$–$C_6$ alkyl);
  $R^3$ is H, alkyl for example, $C_1$–$C_6$ alkyl, or (alkyl)C=O for example, (($C_1$–$C_6$)alkyl)-C=O;
  $R^4$ and $R^5$ are independently H, halogen (F, Cl, Br or I), alkyl, for example $C_1$–$C_6$ alkyl, alkoxy, such as $C_1$–$C_4$ alkoxy, nitro, amino, cyano, carboxyl or acyl which may be substituted for one or more hydrogens on the ring;
  X is —$OR^6$, —$NR^7R^8R^9$, —$NCOR^{10}$, —$NO_2$, —$SR^{11}$
  wherein,
    $R^6$ and $R^{11}$ are independently selected from H, alkyl, substituted alkyl, cycloalkyl, substituted cycloalkyl, aryl, substituted aryl, acyl, for example $C_1$–$C_6$ acyl such as —C(O)—$C_1$–$C_6$ alkyl or aroyl,
    $R^7$, $R^8$ and $R^{10}$ are independently selected from hydrogen, alkyl, substituted alkyl, cycloalkyl, substituted cycloalkyl, aryl, or substituted aryl,
    $R^9$ and $R^{12}$ can be present or absent and are independently selected from hydrogen, alkyl, substituted alkyl, cycloalkyl, substituted cycloalkyl, aryl, or substituted aryl
and phamaceutically acceptable salts thereof.

In a particular embodiment, the naltrexone analog is:

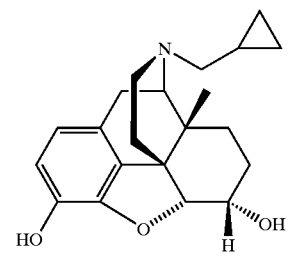

6α-Naltrexol

-continued

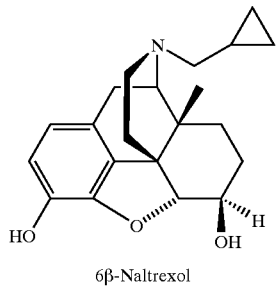
6β-Naltrexol

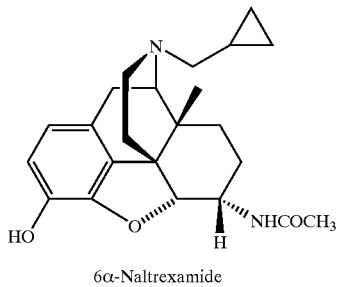
6α-Naltrexamide

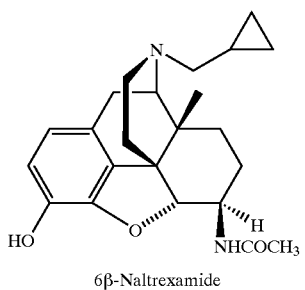
6β-Naltrexamide

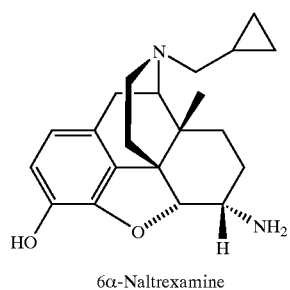
6α-Naltrexamine

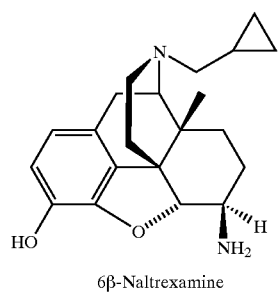
6β-Naltrexamine and the pharmaceutically acceptable salts thereof.

The naloxone analog suitable for use in the method of the invention can be represented by Formula I:

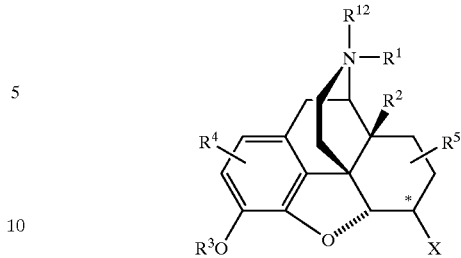

wherein:

$R^1$ is alkenyl, for example a $C_3$–$C_6$ alkenyl, such as allyl $R^2$ is H, OH or esters thereof, such as —OAc(O$_2$C(alkyl)), for example O$_2$(C$_1$–C$_6$ alkyl);

$R^3$ is H, alkyl for example, C$_1$–C$_6$ alkyl, or (alkyl)C=O for example, ((C$_1$–C$_6$)alkyl)-C=O;

$R^4$ and $R^5$ are independently H, halogen (F, Cl, Br or I), alkyl, for example C$_1$–C$_6$ alkyl, alkoxy, such as C$_1$–C$_4$ alkoxy, nitro, amino, cyano, carboxyl or acyl which may be substituted for one or more hydrogens on the ring;

X is —OR$^6$, —NR$^7$R$^8$R$^9$, —NCOR$^{10}$, —NO$_2$, —SR$^{11}$;

wherein, $R^6$ and $R^{11}$ are independently selected from H, alkyl, substituted alkyl, cycloalkyl, substituted cycloalkyl, aryl, substituted aryl, acyl, for example C$_1$–C$_6$ acyl such as —C(O)—C$_1$–C$_6$ alkyl or aroyl, $R^7$, $R^8$ and $R^{10}$ are independently selected from hydrogen, alkyl, substituted alkyl, cycloalkyl, substituted cycloalkyl, aryl, or substituted aryl, $R^9$ and $R^{12}$ can be absent or present and are independently selected from hydrogen, alkyl, substituted alkyl, cycloalkyl, substituted cycloalkyl, aryl, or substituted aryl and phamaceutically acceptable salts thereof.

In a particular embodiment, the naloxone analog is

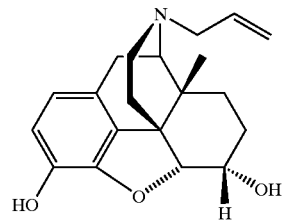
6α-Naloxol

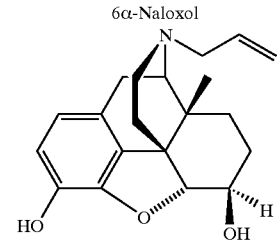
6β-Naloxol

-continued

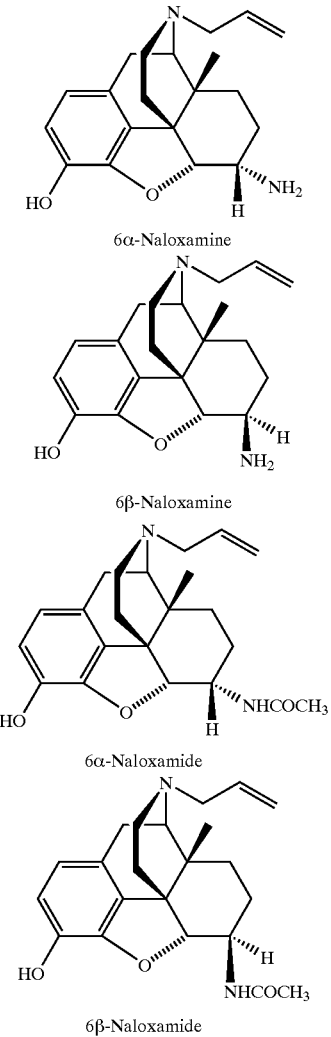

6α-Naloxamine

6β-Naloxamine

6α-Naloxamide

6β-Naloxamide and pharmaceutically acceptable salts thereof.

In one embodiment, the drug-dependent individual is in long-term therapy to prevent relapse to drug use. In another embodiment, the drug-dependent individual is undergoing active withdrawal treatment. In yet another embodiment, the drug-dependent individual is undergoing acute treatment for a drug overdose. In a further embodiment, the drug-dependent individual is an infant born to a drug-addicted mother. In another embodiment, the individual is being administered opiate drugs for the treatment of pain as part of an anesthetic regimen.

The invention further relates to a method for the treatment of drug-dependency in a drug-dependent individual in need thereof comprising administering to the individual a therapeutically effective amount of a sustained release composition comprising a biocompatible polymer and an effective amount of a naloxone or naltrexone analog or the pharmaceutically acceptable salts thereof which is neutral antagonist at the µ opioid receptor. Use of a sustained release composition, as described herein, can be particularly desirable when the drug-dependent individual is under long-term therapy to prevent relapse to the drug of abuse.

The invention also relates to a kit, useful for treating drug dependency in a drug-dependent individual comprising a therapeutically effective dose of a naloxone or naltrexone analog, which is a neutral antagonist at the µ opioid receptor, and instructional materials associated with the dose. The kit is useful in the treatment of all drug dependent individuals such as those in long-term therapy to prevent relapse, individuals undergoing drug overdose treatment, individuals undergoing active withdrawal treatment and infants born to drug addicted mothers.

Therefore, agents which can be used in the treatment of drug dependency and in pain management but which have reduced aversive properties and can result in reduced withdrawal symptoms are provided by the present invention. Further, the agents described herein can be useful in a pain management regimen to modify the anesthesia/analgesia of an opioid drug or its undesirable side effects. In addition, the naltrexone and naloxone analogs described herein can be suitable for use in the treatment of eating disorders.

Figure 1:
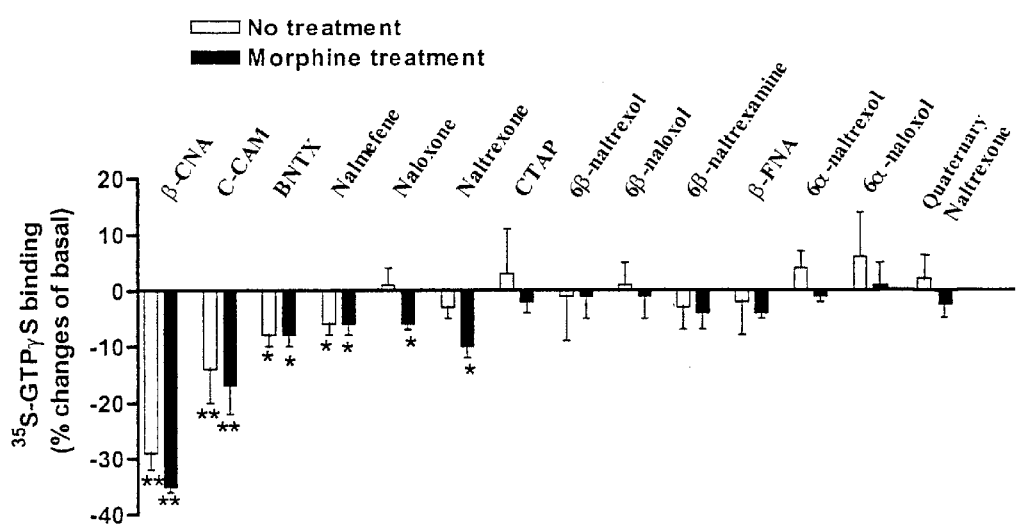
FIG. 1 is a graph showing results of the indicated opioid antagonists on the $^{35}$S-GTPγS binding to HEK-MOR cell membranes to determine the intrinsic antagonist activity. Mean±SD, *, ** versus % changes of basal done with mock-transfected cells. P<0.05, P<0.01, respectively, n=6, ANOVA with Dunnett post test.

The foregoing and other objects, features and advantages of the invention will be apparent from the following more particular description of preferred embodiments of the invention, and as illustrated in the accompanying drawings.

DETAILED DESCRIPTION OF THE INVENTION

A description of preferred embodiments of the invention follows.

The present invention relates to a method for the treatment of drug-dependency in a drug-dependent individual in need thereof comprising administering to the individual a therapeutically effect amount of a naloxone or naltrexone analog or a pharmaceutically acceptable salt thereof which is a neutral antagonist at the µ opioid receptor.

The naltrexone analogs suitable for use in the invention can be represented by Formula I and includes the pharmaceutically acceptable salts thereof:

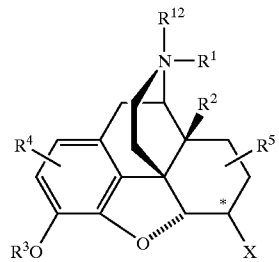

wherein:
- $R^1$ is (cycloalkyl)alkyl, for example, $C_3$–$C_6$ (cycloalkyl) alkyl, for example, $C_3$–$C_6$(cycloalkyl)methyl such as (cyclopropyl)methyl or (cycloalkenyl)alkyl, for example, $C_5$–$C_7$(cycloalkenyl)alkyl;
- $R^2$ is H, OH or esters thereof, such as —OAc($O_2C$ alkyl), for example $O_2(C_1$–$C_6)$alkyl;
- $R^3$ is H, alkyl for example, $C_1$–$C_6$ alkyl, or (alkyl)C=O for example, (($C_1$–$C_6$)alkyl)-C=O;
- $R^4$ and $R^5$ are independently H, halogen (F, Cl, Br or I), alkyl, for example $C_1$–$C_6$ alkyl, alkoxy, such as $C_1$–$C_4$ alkoxy, nitro, amino, cyano, carboxyl or acyl which can be substituted for any hydrogen on the ring;
- X is —$OR^6$, —$NR^7R^8R^9$, —$NCOR^{10}$, —$NO_2$, —$SR^{11}$;

wherein,
- $R^6$ and $R^{11}$ are independently selected from H, alkyl, substituted alkyl, cycloalkyl, substituted cycloalkyl, aryl, substituted aryl, acyl, for example $C_1$–$C_6$ acyl such as —C(O)—$C_1$–$C_6$ alkyl or aroyl,
- $R^7$, $R^8$ and $R^{10}$ are independently selected from hydrogen, alkyl, substituted alkyl, cycloalkyl, substituted cycloalkyl, aryl, or substituted aryl,
- $R^9$ and $R^{12}$ can be absent or present are independently selected from hydrogen, alkyl, substituted alkyl, cycloalkyl, substituted cycloalkyl, aryl, or substituted aryl and phamaceutically acceptable salts thereof.

In a particular embodiment, the naltrexone analog is:

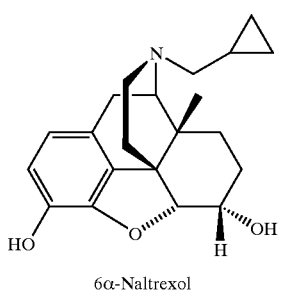

6α-Naltrexol

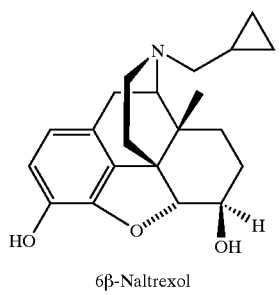

6β-Naltrexol

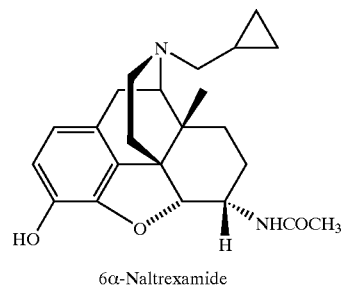

6α-Naltrexamide

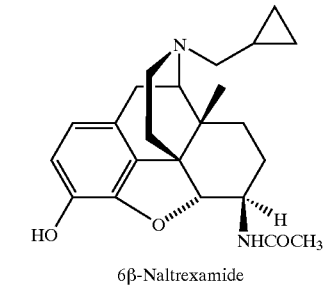

6β-Naltrexamide

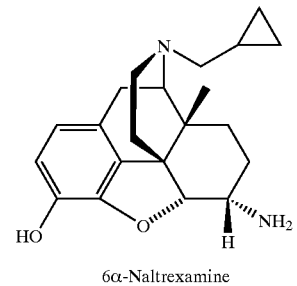

6α-Naltrexamine

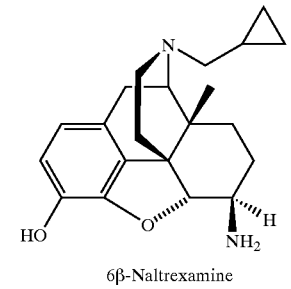

6β-Naltrexamine and the pharmaceutically acceptable salts thereof.

The naloxone analog suitable for use in the method of the invention can be represented by Formula I:

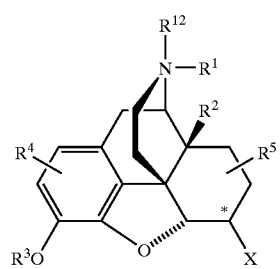

wherein:

R¹ is alkenyl, for example a $C_3$–$C_6$ alkenyl, such as allyl

R² is H, OH or esters thereof, such as —OAc($O_2$C alkyl), for example $O_2$($C_1$–$C_6$)alkyl;

R³ is H, alkyl for example, $C_1$–$C_6$ alkyl, or (alkyl)C=O for example, (($C_1$–$C_6$)alkyl)-C=O;

R⁴ and R⁵ are independently H, halogen (F, Cl, Br or I), alkyl, for example $C_1$–$C_6$ alkyl, alkoxy, such as $C_1$–$C_4$ alkoxy, nitro, amino, cyano, carboxyl or acyl which can be substituted for one or more hydrogens on the ring;

X is —OR⁶, —NR⁷R⁸R⁹, —NCOR¹⁰, —$NO_2$, —SR¹¹ wherein,

R⁶ and R¹¹ are independently selected from H, alkyl, substituted alkyl, cycloalkyl, substituted cycloalkyl, aryl, substituted aryl, acyl, for example $C_1$–$C_6$ acyl such as —C(O)—$C_1$–$C_6$ alkyl or aroyl, R⁷, R⁸ and R¹⁰ are independently selected from hydrogen, alkyl, substituted alkyl, cycloalkyl, substituted cycloalkyl, aryl, or substituted aryl R⁹ and R¹² can be absent or present are independently selected from hydrogen, alkyl, substituted alkyl, cycloalkyl, substituted cycloalkyl, aryl, or substituted aryl and phamaceutically acceptable salts thereof.

In a particular embodiment, the naloxone analog is

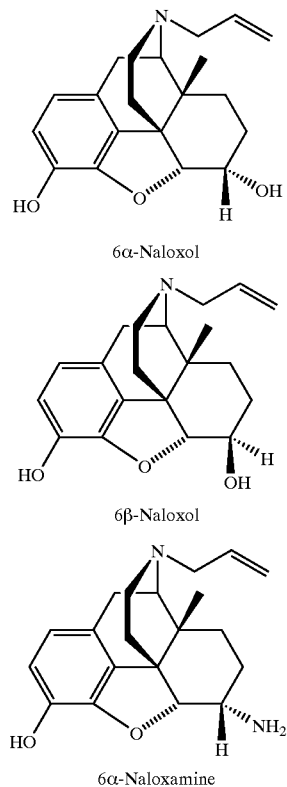

6α-Naloxol

6β-Naloxol

6α-Naloxamine

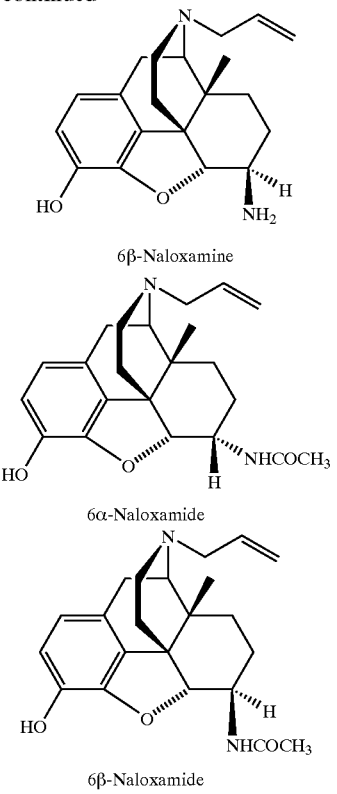

6β-Naloxamine

6α-Naloxamide

6β-Naloxamide and pharmaceutically acceptable salts thereof.

Pharmaceutically acceptable salts of the naltrexone and naloxone analogs, which are neutral antagonists at the μ opioid receptor, include salts derived from an appropriate base, such as an alkali metal (for example, sodium, potassium), an alkaline earth metal (for example, calcium, magnesium), ammonium and $NX_4^+$ (wherein X is $C_1$–$C_4$ alkyl). Pharmaceutically acceptable salts of an amino group include salts of: organic carboxylic acids such as acetic, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of a compound having a hydroxy group consist of the anion of said compound in combination with a suitable cation such as $Na^+$, $NH_4^+$, or $NX_4^+$ (wherein X is for example a $C_{1-4}$ alkyl group).

In enantiomeric forms, compounds of the invention include individual enantiomers of the compounds of formula (I) in single species form substantially free of the corresponding enantiomer, as well as in admixture (in mixtures of enantiomeric pairs and/or in mixtures of multiple enantiomer species). In the compounds described herein the terms α and β anomers are used to distinguish the orientation of the subsitutuents at the chiral carbon marked with an (*).

The drug-dependent individual can be dependent upon one or multiple drug substances. Drug substances which can cause a dependency treatable by the method described herein include, but are not limited to, opioids, alcohol, stimulants, depressants, nicotine, designer drugs, sedative hypnotics, hallucinogens, angiolytics and inhalants.

Extension of the use of the naloxone and naltrexone analogs, which are neutral antagonists at μ opioid receptor, for treatment of dependency on the classes of drug substances set forth above is predicated on studies which report that addiction to cocaine and alcohol can involve opioid-sensitive brain cell networks (See, Gardner et al., *Substance Abuse* $2^{nd}$ *Ed.*, pp. 70–99 (1992)). As such, the use of opioid antagonists can be suitable for use in the treatment of drugs other than opioids such as the commonly abused drugs, alcohol and cocaine. In addition, the naltrexone and naloxone analogs of the present invention can be useful in the treatment of eating disorders.

Opiates, are a class of centrally acting compounds and are frequently used agents for pain control. Opiates are narcotic agonistic analgesics and are drugs derived from opium, such as morphine, codeine, and many synthetic congeners of morphine, with morphine being the most widely used derivative. Opioids are natural and synthetic drugs with morphine-like actions and include the opiates. Opioids are narcotic agonistic analgesics which produce drug dependence of the morphine type and are subject to control under federal narcotics law because of their addicting properties.

The chemical classes of opioids with morphine-like activity are the purified alkaloids of opium consisting of phenanthrenes and benzylisoquinolines, semi-synthetic derivatives of morphine, phenylpiperidine derivatives, morphinan derivatives, benzomorphan derivatives, diphenyl-heptane derivatives, and propionanilide derivatives. The principal phenanthrenes are morphine, codeine, and thebaine. The principal benzoisoquinolines are papaverine, a smooth muscle relaxant, and noscapine. Semi-synthetic derivatives of morphine include diacetylmorphine (heroin), hydromorphone, oxymorphone, hydrocodone, apomorphine, etorpine, and oxycodone. Phenylpiperidine derivatives include meperidine and its congeners diphenoxylate and loperamide, alphaprodine, anileridine hydrochloride or phosphate, and piminodine esylate. Morphinan derivatives include levorphanol. The diphenyl-heptane derivatives include methadone and its congeners, and propoxyphene. Propionanilide derivatives include fentanyl citrate and its congeners sufenil citrate and alfenatil hydrochloride.

Stimulants include, but are not limited to, amphetamines, cocaine, phenmetrazine, methylphenidate.

Depressants include, but are not limited to, nonbarbiturates, methaqualone, barbiturates, diazepam, flurazepam, phencyclidine and fluoxetine.

Designer drugs include, for example, ecstasy (methylenedioxymethamphetamine (MDMA)) which has both stimulant and hallucinogenic effects.

"Drug-dependent individual" as that term is used herein refers to the recipient of the treatment described herein and includes individuals in long-term therapy to prevent relapse to drug use, individuals who have taken an overdose of a drug and are in need of acute treatment, individuals who are undergoing active withdrawal treatment from addiction and infants born to drug addicted mothers. Mammalian and non-mammalian patients are included. In a specific embodiment, the patient is a mammal, such as a human, canine, murine, feline, bovine, ovine, swine or caprine. In a preferred embodiment, the patient is a human. It is understood that the drug-dependent individual can be dependent upon multiple drugs.

In an alternative embodiment, the naltrexone and naloxone antagonists are suitable for use in the management of pain, for example, short term pain following surgery or injury, during and after anesthesia, or during long-term pain treatment. A shown in FIG. 4, naloxone and naltrexone have aversive effects (withdrawal jumping) in mice even after a single dose of morphine related to the presence of the basally active $\mu$ opioid receptor. Therefore, this type of inverse agonist is not suitable for modifying side effects of opioid drugs (e.g., respiratory depression). However, the naloxone and naltrexone analogs described herein which are neutral antagonist can be used to diminish side effects without causing adverse effects themselves. Alternatively, the naloxone and naltrexone analogs described herein can be useful in diminishing constipation which is a common and limiting side effect frequently resulting from administration of an opioid agonist in pain management. That is the opioid interacts with the opioid receptors in the gastrointestinal tract (peripheral action). Further, it is noted that in the chronic mouse model of morphine dependence used to observe withdrawal jumping, no diarrhea was observed with administration of neutral antagonist. Therefore neutral antagonists that remain either partially or completely in the peripheral circulation, as opposed to the CNS (central nervous system) circulation, can be suitable in reducing constipation without causing diarrhea (as, for example, naloxone can be expected to do).

In a further embodiment, the naltrexone and naloxone analogs are suitable for use in the treatment of eating disorders.

As used herein, a "therapeutically effective amount" refers to the amount of the naltrexone or naloxone analog or sustained release composition having the naltrexone or naloxone analog incorporated therein, needed to elicit the desired biological response following administration. The desired biological response herein can be sufficient blockade of the $\mu$ opioid receptor resulting in alleviation of drug dependency, modulation of pain management or reducing adverse effects associated with current pain management such as diarrhea and constipation.

Therapeutically effective amounts of the neutral antagonists can be formulated as pharmaceutically suitable compositions (e.g. in the form of pharmaceutically acceptable salts). In the treatment of an overdose, for example, the amount of naltrexone or naloxone analog needed can be comparable to that currently used for naloxone, in treating individuals who have taken a narcotic overdose. In the treatment of an individual in long-term or maintenance therapy, the amounts effective in preventing drug use resumption are similar to those prescribed for naltrexone. A therapeutically effective amount can be in the range of about 1 microgram ($\mu$g) to about 100 milligrams (mg) per kilogram of body weight of the recipient per day. For example, from about 5 $\mu$g to about 75 mg per kilogram body weight per day, such as from about 10 $\mu$g to about 50 mg per kilogram body weight per day. The administered dose can be present as two or more sub-doses administered at appropriate intervals throughout the day. Alternatively, if the condition of the drug-dependent individual requires the doses can be administered as continuous infusion.

The composition of this invention can be administered in vivo, for example, to a drug dependent individual, for example, a human, or an animal. In a preferred embodiment, the naltrexone and naloxone analogs, which are neutral antagonists at the $\mu$ opioid receptor act centrally when administered peripherally. Alternatively, a neutral antagonist can also be administered peripherally and in large part retained in the peripheral circulation (e.g., in the gastrointestinal tract). Such neutral antagonists can have potent peripheral activity but lesser central activity. Administration can be accomplished orally, or parenterally such as by injection, implantation (e.g., subcutaneously, intramuscularly, intraperitoneally, intracranially, and intradermally), administration to mucosal membranes (e.g., intranasally, intravaginally, intrapulmonary, buccally or by means of a suppository), or in situ delivery (e.g., by enema or aerosol spray) to provide the desired dosage of naltrexone or naloxone analog to treat drug dependency or modulate undesirable effects of narcotic analgesic (such as respiratory depression and constipation) in the treatment of pain or anesthesia, in an individual in need thereof.

"Neutral antagonists" as that term is used herein, refers to agents which block the affects of an agonist at the target receptor, but do not significantly effect the level of spontaneous activity present at the target receptor. "Neutral antagonist at the $\mu$ opioid receptor" as that term is used herein refers to an agent which can bind selectively to the resting, drug-sensitive $\mu$ opioid receptor state, to the constitutively active $\mu$ opioid receptor state, or to both, blocking the effects of an agonist at the receptor, but not significantly effecting the level of spontaneous activity present at the receptor.

"Partial inverse agonists", as that term is used herein refers to agents which block the affects of an agonists at the target receptor and also suppress spontaneous receptor activity at the target receptor.

"Full inverse agonist" as that term is used herein refers to an agent that suppresses completely spontaneous receptor activity at the target receptor and will also block the affects of an agonist at the target receptor.

"Partial agonists" as that term is used herein refers to agents that induce an agonist response, for example, receptor activation, but even at maximal dosages result in only partial activation of the resting, drug-sensitive target receptor.

The naloxone and naltrexone analogs represented by the structures presented herein can be synthesized using standard synthetic procedures such as those described in *March J., Advanced Organic Chemistry*, $3^{rd}$ *Ed.* (1985). Employing, for example, naltrexone or naloxone as the starting material.

Many of the analogs of naltrexone and naloxone which possess neutral antagonist activity at the $\mu$ opioid receptor, for example, the analogs wherein the 6-keto functionality has been reduced to an —OH functionality are known compounds, and their syntheses have been described, for example, by Chatterjie et al., *J. Med. Chem.*, 18, pp. 490–492 (1975) and Jiang et al., *J. Med. Chem.*, 20, pp. 1100–1102 (1977). When modification of the naltrexone or naloxone at the 6-keto position results in an additional chiral carbon in the analog, the β orientation at the newly formed chiral carbon is preferred over the α orientation. This preference is based upon the slower conversion of the β analogs back to naloxone or naltrexone. Further, if desired conversion of the naltrexone or naloxone analog can be blocked by any suitable inhibitory agent. For example, in the case of 6β- or 6α-naloxol or naltrexol, conversion of the —OH at the 6 position back to the keto functionality of the naloxone or naltrexone can be inhibited with alcohol dehydrogenase inhibitors, such as 4-methylpyrazole (Plapp, B. V., "Control of Alcohol Metabolism," pp. 311–322 in *Towards a Molecular Basis of Alcohol Use and Abuse*, eds. Janssen et al., Birkhaeuser Verlag, 1994). Further, the replacement of the 6-keto functionality with, for example, an amine or amide resulting in 6α- and 6β-naltrexamine and naltrexamide is likely to undergo much slower, if any, conversion to naltrexone.

As used herein, in reference to the present invention, the term "alkyl" is intended to be broadly construed as encompassing: (i) alkyl groups of straight-chain as well as branched chain character; (ii) unsubstituted as well as substituted alkyl groups, wherein the substitutents of substituted alkyl groups may include any substituents which are compatible with such alkyl and which retain the neutral antagonistic behavior of the naloxone and naltrexone analogs. Examples of substituents for substituted alkyl groups include halogen, for example, fluoro, chloro, bromo and iodo, amino, amido, $C_1$–$C_4$ alkyl, $C_1$–$C_4$ alkoxy, nitro, hydroxy; (iii) saturated alkyl groups as well as unsaturated alkyl groups, the later including groups such as alkenyl substituted alkyl, for example, allyl, methallyl, propallyl, butenylmethyl, etc. Alkynyl substituted alkyl groups and any other alkyl groups containing unsaturation which is compatible with such alkyl groups and which retains the neutral antagonistic behavior of the naloxone and naltrexone analogs; and (iv) alkyl groups including linking or bridge moieties, for example, heteroatoms such as nitrogen, oxygen, sulfur.

As used herein, in reference to the present invention, the term aryl is intended to be broadly construed as referring to carbocyclic, for example, phenyl, naphthyl as well as heterocyclic aromatic groups, for example pyridyl, thienyl, furanyl and encompassing unsubstituted as well as substituted aryl groups, wherein the substituents of the substituted aryl groups can include any substituents which retain the neutral antagonistic behavior of the naloxone and naltrexone analogs. Examples of substituents for substituted aryl groups include one or more of halogen, for example, fluoro, chloro, bromo and iodo, amino, amido, $C_1$–$C_4$ alkyl, $C_1$–$C_4$ alkoxy, nitro, trifluoromethyl, hydroxy, hydroxyalkyl containing a $C_1$–$C_4$ alkyl moiety, etc.

The invention also relates to a kit, useful for treating drug dependency in a drug-dependent individual comprising a therapeutically effective dose of a naloxone or naltrexone analog, which is a neutral antagonist at the $\mu$ opioid receptor, and instructional materials associated with the dose. The kit is useful in the treatment of all drug dependent individuals such as those in long-term therapy to prevent relapse, individuals undergoing drug overdose treatment, individuals undergoing active withdrawal treatment and infants born to drug addicted mothers.

For example, the kit can comprise a container containing a suitable neutral antagonist and, in addition, the kit can include instructional materials containing directions (for example, dosage protocols) for the administration of the pharmaceutically effective compositions described here along with contraindications. Information on the withdrawal syndrome activity of the particular neutral antagonist present in the kit can also be included in the instructional materials. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to Internet sites that provide such instructional materials.

As used herein, the term "a" or "an" refers to one or more.

Method for Sustained Release

In another embodiment, the invention relates to a method for the treatment of drug-dependency in a drug-dependent individual in need thereof comprising administering to the individual a therapeutically effect amount of a sustained release composition comprising a biocompatible polymer; and an effective amount of a naloxone or naltrexone analog or the pharmaceutically acceptable salts thereof which is neutral antagonist at the $\mu$ opioid receptor.

The term "sustained release composition" as defined herein, can comprise a biocompatible polymer having incorporated therein at least one naloxone or naltrexone analog which is a neutral antagonist at the $\mu$ opioid receptor. Suitable biocompatible polymers, can be either biodegradable or non-biodegradable polymers or blends or copolymers thereof, as described herein. Use of a sustained release composition, as described herein, can be particularly advantageous when the drug-dependent individual is under long-term therapy to prevent relapse to the drug of abuse.

Typically, the sustained release composition can contain from about 0.01% (w/w) to about 50% (w/w) of the naloxone or naltrexone analog which is a neutral antagonist at the $\mu$ opioid receptor (dry weight of composition). The amount of naloxone or naltrexone analog used will vary depending upon the condition of the patient, the desired effect of the agent, for example, to treat active withdrawal or to prevent relapse in long-term therapy, the planned release levels, and the time span over which the agent will be released. A preferred range of agent loading is between about 0.1% (w/w) to about 30% (w/w) agent. A more preferred range of agent loading is between about 0.5% (w/w) to about 20% (w/w) agent.

The sustained release compositions of this invention can be formed into many shapes such as a film, a pellet, a rod, a filament, a cylinder, a disc, a wafer or a microparticle. A microparticle is preferred. A "microparticle" as defined herein, comprises a polymer component having a diameter of less than about one millimeter and having a naltrexone or naloxone analog which is a neutral antagonist at the $\mu$ opioid receptor dispersed therein. A microparticle can have a spherical, non-spherical or irregular shape. Typically, the microparticle will be of a size suitable for injection. A preferred size range for microparticles is from about one to about 180 microns in diameter.

As defined herein, a sustained release of a naltrexone or naloxone analog of the present invention is a release of the agent from a sustained release composition. The release occurs over a period which is longer than that period during which a therapeutically significant amount of the naloxone or naltrexone analog, would be available following direct administration of a solution of the analog. The period of sustained release can be, for example, about one day, about two days, about seven days, about ten days or more as needed to attain the desired results. It is preferred that a sustained release be a release of naloxone or naltrexone analog, which is a neutral antagonist at the $\mu$ opioid receptors, which occurs over a period of greater than two days. A sustained release of a naltrexone or naloxone analog of the invention, from a sustained release composition can be a continuous or a discontinuous release, with relatively constant or varying rates of release. The continuity of release and level of release can be affected by the type of polymer composition used (e.g., monomer ratios, molecular weight, and varying combinations of polymers), agent loading, and/or selection of excipients to produce the desired effect.

The polymers of the sustained release composition described herein are biocompatible. Suitable biocompatible polymers, can be either biodegradable or non-biodegradable polymers or blends or copolymers thereof, as described herein.

Suitable biocompatible polymers, can be either biodegradable or non-biodegradable polymers or blends or copolymers thereof, as described herein. A polymer is biocompatible if the polymer and any degradation products of the polymer are non-toxic to the recipient and also possess no significant deleterious or untoward effects on the recipient's body, such as an immunological reaction at the injection site.

"Biodegradable", as defined herein, means the composition will degrade or erode in vivo to form smaller chemical species. Degradation can result, for example, by enzymatic, chemical and physical processes. Suitable biocompatible, biodegradable polymers include, for example, poly (lactides), poly(glycolides), poly(lactide-co-glycolides), poly(lactic acid)s, poly(glycolic acid)s, polycarbonates, polyesteramides, polyanydrides, poly(amino acids), polyorthoesters, poly(dioxanone)s, poly(alkylene alkylate)s, copolymers or polyethylene glycol and polyorthoester, biodegradable polyurethane, blends thereof, and copolymers thereof.

Suitable biocompatible, non-biodegradable polymers include non-biodegradable polymers selected from the group consisting of polyacrylates, polymers of ethylene-vinyl acetates and other acyl substituted cellulose acetates, non-degradable polyurethanes, polystyrenes, polyvinylchloride, polyvinyl flouride, poly(vinyl imidazole), chlorosulphonate polyolefins, polyethylene oxide, blends thereof, and copolymers thereof.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weight is of about 2,000 Daltons to about 2,000,000 Daltons.

In a particular embodiment, the polymer is biodegradable polymer or copolymer. In a more preferred embodiment, the polymer is a poly(lactide-co-glycolide)(hereinafter "PLG"). The PLG can have a lactide:glycolide ratio, for example, of about 10:90, 25:75, 50:50, 75:25 or 90:10 and a molecular weight of about 5,000 Daltons to about 70,000 Daltons.

It is understood that when the naltrexone or naloxone analog, which is a neutral antagonist at the $\mu$ opioid receptor, is incorporated into a biocompatible polymer for sustained release of the analog, the sustained release composition can include additional components which can stabilize the analog and/or modify the release profile of the naltrexone or naloxone analog from the sustained release composition. That is, the naltrexone or naloxone analog of the sustained release composition can be stabilized against loss of potency and/or loss of activity, all of which can occur during formation of the sustained release composition having the naltrexone or naloxone analog dispersed therein, and/or prior to and during in vivo release of the analog. In addition, the period of release of the naltrexone or naloxone analog can be prolonged.

A suitable excipient or a specific combination of excipients can be employed in the sustained release composition. "Excipient", as that term is used herein, is any agent which binds or interacts in a covalent or non-covalent manner or is included with the naloxone or naltrexone analog in the sustained release composition.

Suitable excipients include, for example, carbohydrates, amino acids, fatty acids, surfactants, and bulking agents, and are known to those skilled in the art. An acidic or a basic excipient is also suitable. The amount of excipient used is based on ratio to the naltrexone or naloxone analog, on a weight basis. For amino acids, fatty acids and carbohydrates, such as sucrose, trehalose, lactose, mannitol, dextran and heparin, the ratio of carbohydrate to analog, is typically between about 1:10 and about 20:1. For surfactants the ratio of surfactant to analog is typically between about 1:1000 and about 2:1. Bulking agents typically comprise inert materials. Suitable bulking agents are known to those skilled in the art.

The excipient can also be a metal cation component which acts to modulate the release of the naltrexone or naloxone analog. A metal cation component used in modulating release typically comprises at least one type of multivalent metal cation. Examples of metal cation components suitable to modulate release include or contain, for example, $Mg(OH)_2$, $MgCO_3$ (such as $4MgCO_3 \cdot Mg(OH)_2 \cdot 5H_2O$), $MgSO_4$, $Zn(OAc)_2$, $Mg(OAc)_2$, $ZnCO_3$ (such as $3Zn(OH)_2 \cdot 2ZnCO_3)ZnSO_4$, $ZnCl_2$, $MgCl_2$, $CaCO_3$, $Zn_3(C_6H_5O_7)_2$ and $Mg_3(C_6H_5O_7)_2$. A suitable ratio of metal cation component to polymer is between about 1:99 to about 1:2 by weight. The optimum ratio depends upon the polymer and the metal cation component utilized. A polymer matrix containing a dispersed metal cation component to modulate the release of a an agent from the polymer matrix is further described in U.S. Pat. No. 5,656,297 to Bernstein et al. the teachings of which are incorporated herein by reference in their entirety.

A number of methods are known by which sustained release compositions (polymer/active agent matrices) can be formed. In many of these processes, the material to be encapsulated is dispersed in a solvent containing a wall forming material. At a single stage of the process, solvent is removed from the microparticles and thereafter the microparticle product is obtained.

Methods for forming a composition for the sustained release of biologically active agent are described in U.S. Pat. No. 5,019,400, issued to Gombotz et al., and issued U.S. Pat. No. 5,922,253 issued to Herbert et al. the teachings of which are incorporated herein by reference in their entirety.

In this method, a mixture comprising a biologically active agent, a biocompatible polymer and a polymer solvent is processed to create droplets, wherein at least a significant portion of the droplets contains polymer, polymer solvent and the active. These droplets are then frozen by a suitable means. Examples of means for processing the mixture to form droplets include directing the dispersion through an ultrasonic nozzle, pressure nozzle, Rayleigh jet, or by other known means for creating droplets from a solution.

Means suitable for freezing droplets include directing the droplets into or near a liquified gas, such as liquid argon or liquid nitrogen to form frozen microdroplets which are then separated from the liquid gas. The frozen microdroplets are then exposed to a liquid or solid non-solvent, such as ethanol, hexane, ethanol mixed with hexane, heptane, ethanol mixed with heptane, pentane or oil.

The solvent in the frozen microdroplets is extracted as a solid and/or liquid into the non-solvent to form a polymer/active agent matrix comprising a biocompatible polymer and a biologically active agent. Mixing ethanol with other non-solvents, such as hexane, heptane or pentane, can increase the rate of solvent extraction, above that achieved by ethanol alone, from certain polymers, such as poly(lactide-co-glycolide) polymers.

A wide range of sizes of sustained release compositions can be made by varying the droplet size, for example, by changing the ultrasonic nozzle diameter. If the sustained release composition is in the form of microparticles, and very large microparticles are desired, the microparticles can be extruded, for example, through a syringe directly into the cold liquid. Increasing the viscosity of the polymer solution can also increase microparticle size. The size of the microparticles which can be produced by this process ranges, for example, from greater than about 1000 to about 1 micrometers in diameter.

Yet another method of forming a sustained release composition, from a suspension comprising a biocompatible polymer and a biologically active agent, includes film casting, such as in a mold, to form a film or a shape. For instance, after putting the suspension into a mold, the polymer solvent is then removed by means known in the art, or the temperature of the polymer suspension is reduced, until a film or shape, with a consistent dry weight, is obtained.

A further example of a conventional microencapsulation process and microparticles produced thereby is disclosed in U.S. Pat. No. 3,737,337, incorporated by reference herein in its entirety, wherein a solution of a wall or shell forming polymeric material in a solvent is prepared. The solvent is only partially miscible in water. A solid or core material is dissolved or dispersed in the polymer-containing mixture and, thereafter, the core material-containing mixture is dispersed in an aqueous liquid that is immiscible in the organic solvent in order to remove solvent from the microparticles.

Another example of a process in which solvent is removed from microparticles containing a substance is disclosed in U.S. Pat. No. 3,523,906, incorporated herein by reference in its entirety. In this process a material to be encapsulated is emulsified in a solution of a polymeric material in a solvent that is immiscible in water and then the emulsion is emulsified in an aqueous solution containing a hydrophilic colloid. Solvent removal from the microparticles is then accomplished by evaporation and the product is obtained.

In still another process as shown in U.S. Pat. No. 3,691,090, incorporated herein by reference in its entirety, organic solvent is evaporated from a dispersion of microparticles in an aqueous medium, preferably under reduced pressure.

Similarly, the disclosure of U.S. Pat. No. 3,891,570, incorporated herein by reference in its entirety, shows a method in which solvent from a dispersion of microparticles in a polyhydric alcohol medium is evaporated from the microparticles by the application of heat or by subjecting the microparticles to reduced pressure.

Another example of a solvent removal process is shown in U.S. Pat. No. 3,960,757, incorporated herein by reference in its entirety.

Tice et al., in U.S. Pat. No. 4,389,330, describe the preparation of microparticles containing an active agent by a method comprising: (a) dissolving or dispersing an active agent in a solvent and dissolving a wall forming material in that solvent; (b) dispersing the solvent containing the active agent and wall forming material in a continuous-phase processing medium; (c) evaporating a portion of the solvent from the dispersion of step (b), thereby forming microparticles containing the active agent in the suspension; and (d) extracting the remainder of the solvent from the microparticles.

Further suitable methods of preparation are described in U.S. Pat. No. 6,194,006 to Lyons et al., U.S. Pat. Nos. 6,110,503, 5,916,598 and 5,792,477 to Rickey et al. and 5,650,173 to Ramstack et al. the entire content of all of which is hereby incorporated by reference.

While this invention has been particularly shown and described with references to preferred embodiments thereof, it will be understood by those skilled in the art that various changes in form and details may be made therein without departing from the scope of the invention encompassed by the appended claims.

Experimental Methods

Materials

Morphine sulfate, 7-benzylidene-7-dehydronaltrexone (BNTX) HCl, naloxone, naltrexone, 6β-naltrexamine, 6β-naltrexol, 6β-naloxol, 6α-naloxol, 6α-naltrexol and 6β-naltrexamide were obtained through the NIDA Drug Supply Program; β-chlornaltrexamine (β-CNA), β-funaltrexamine HCl (β-FNA), N',N'-diallyl-Tyr-Aib-Aib- Phe-Leu (ICI 174 864), [D-Pen$^2$,D-Pen$^5$]-enkephalin (DPDPE) and pertussis toxin (PTX) were purchased from RBI (Natick, Mass.); clocinnamox (C-CAM) was purchased from Tocris Cookson (Ballwin, Mo.); nalmefene was purchased from Key Pharmaceuticals (Miami, Fla.); D-Phe-Cys-Tyr-D-Trp-Arg-Thr-Pen-Thr-Nh2 (CTAP) was purchased from Multiple Peptide Systems (San Diego, Calif.). $^{35}$S-Guanosine 5'-(γ-thio) triphosphate (46.2 TBq/mmol) was purchased from NEN (Boston, Mass.), [2,8-$^3$H]-adenine (1.11 TBq/mmol) from ICN (Costa Mesa, Calif.); AG 50-X8 resin and empty poly-prechromatography columns were purchased from Bio-Rad; and neutral alumina and imidazole were purchased from Sigma (St. Louis, Mo.).

In vitro Testing

Cell Culture

Human embryonic kidney (HEK 293) cells stably transfected with human MOR (N-terminal FLAG-tagged, HEK-MOR) and mouse δ opioid receptor (DOR) (HEK-DOR) were maintained in DMEM H16/F12 supplemented with 10% fetal bovine serum. hMOR-transfected GH$_3$ cells (GH$_3$-MOR) were cultured in the same medium as HEK cells, while rat MOR-transfected CHO cells (CHO-MOR) were maintained in F12 Ham's medium supplemented with 10% fetal bovine serum. All cells were expressing a similar level of receptors (~1 pmol receptor/mg protein, tested by $^3$H-naloxone binding assay) except for GH$_3$-MOR, which had lower receptor density (~150 fmol/mg protein). In all three cell lines, 100 mU/mL penicillin, 100 mg/mL streptomycin and 200 mg/mL G418 were included in the culture medium. The cells were allowed to grow at 37° C. in humidified atmosphere of 5% $CO_2$, 95% air.

For morphine pretreatment, cells were cultured in the presence of morphine (1 mM) for 16 hrs before harvest. For β-CNA and β-FNA pretreatment, cells were incubated with different concentrations of β-CNA and β-FNA for 3 hrs at 37° C. Cells were then washed thoroughly with phosphate buffered saline (PBS) to remove the treated drugs before membrane preparations.

Membrane Preparations and $^{35}$S-GTPγS Binding Studies— General Procedure

Membrane preparations and $^{35}$S-GTPγS binding assays were carried as described in Burford, N. T. et al., *Eur. J. Pharmacol.* 342, 123–126 (1998), with minor modifications. Briefly, the desired cells, maintained as described above, were harvested and washed with PBS. The cells were then homogenized in 10 mM HEPES, pH 7.6 buffer and centrifuged at 30,000 g for 10 min. The pellets were resuspended in buffer containing 10 mM HEPES (pH 7.6), 0.1 mM EDTA and stored at −80° C.

For $^{35}$S-GTPγS binding assay, cell membranes (50 mg protein) were incubated with the desired concentration of drug in 500 mL assay buffer (50 mM HEPES, pH 7.4, 100 mM NaCl, 1 mM EDTA, 10 μMGDP, 1 mM DTT, 0.2 nM $^{35}$S-GTPγS, 0.1% bovine serum album and different concentrations of MgCl$_2$) at 30° C. for 20 min. It was determined that the optimum concentration of MgCl$_2$ varied based on the cell line being employed. The reactions were stopped by centrifugation at 13,000 g for 10 min and membranes were washed once with 50 mM Tris-HCl, pH 7.4, 50 mM NaCl. Morphine-stimulated $^{35}$S-GTPγS binding assays were carried out in the presence of 10 mM MgCl$_2$ at 30° C. for 5 min.

EXAMPLE 1

Identification of Neutral Antagonists: Effects of MOR Antagonists on $^{35}$S-GTPγS Binding Activity in HEK-MOR Cell Membranes with or without Morphine Pretreatment Opioid antagonists were tested for their effect on $^{35}$S-GTPγS binding according to the assay described above and further described in Wang et al., *J. Biol. Chem.*, 274, p 22081–22088 (1999). The results of this assay are a direct measure of receptor signalling. More specifically, the cell membranes used were HEK-MOR cell membranes and the assay was conducted in the absence of any agonist to determine the intrinsic antagonist activity. The experiments were done with 1 mM MgCl$_2$ added to the reaction mixture, using untreated and morphine-pretreated HEK-MOR cell membranes. The results are represented graphically in FIG. 1. The amount of drug used was 1 μM. None of the compounds tested had any measurable effect in mock-transfected control cells.

The compounds tested fell into three groups. The first group (β-CNA, C-CAM, BNTX and nalmefene) decreased $^{35}$S-GTPγS binding activity in both untreated and morphine-pretreated HEK-MOR membranes. In view of these results it was concluded that these agents were inverse agonists under any condition. The most effective inverse agonist was β-CNA which has been reported previously by Burford, N. et al., *Biochem. J.* 348, 531–537 and Wang, D. et al. *J. Neurochem.*, 75, 763–771. C-CAM, a MOR-selective antagonist as described by Comer, S. D. et al., *J. Pharmacol. Exp. Ther.*, 262, 1051–1056 (1992), and BNTX, a DOR-selective antagonist as described by Palmer, R. B. et al., *J. Med. Chem.*, 40, 749–753., had already been shown to be inverse agonists at DOR (Neilan, C. L. et al., *Bri. J. Pharmacol.* 128, 556–562 (1999). Dose-response curves for β-CNA ($^{35}$S-GTPγS binding) revealed a twofold difference in naive and morphine-pretreated HEK-MOR cell membranes (EC$_{50}$ values of 29±3 nM and 59±6 nM, respectively).

The second group, naloxone and naltrexone, displayed no observable effects in untreated membranes, but decreased $^{35}$S-GTPγS binding activity in morphine pretreated membranes. This is consistent with our previous reports showing naloxone has little effect in untreated cells, but turns into an inverse agonist in morphine pretreated SH-SY5Y cells (Wang, Z. et al., *Life Sci.*, 54, L339-PL350, (1994)).

The remaining 7 compounds belong to a third group, which had no significant effect on basal $^{35}$S-GTPγS binding activity in both untreated and morphine pretreated membranes. Acting as neutral antagonists under each condition, these compounds include the naloxone and naltrexone analogues, 6α-naloxol, 6β-naloxol, 6α-naltrexol, 6β-naltrexol and 6α-naltrexamine, CTAP and β-FNA.

In addition to the compounds set forth in FIG. 1, 6β-naltrexamide was also tested. Results confirm that 6β-naltrexamide is a neutral antagonists since it had no significant effect on basal $^{35}$S-GTPγS binding activity in both untreated and morphine pretreated membranes. In all assays, 6β-naltrexamide behaved similarly to 6β-naltrexamine.

Neutral antagonists are expected to block the effects of both agonists and inverse agonists. Indeed, the inverse agonistic effects of 1 μM β-CNA and C-CAM were partially or fully blocked by 10 μM 6β-naltrexol (% inhibition: 68±17% and 91±9% for β-CNA and C-CAM respectively, n=3). CTAP and α-naloxol (both at a 10 μM concentration) also blocked the inverse-agonistic effects of β-CNA. This result confirmed that the inverse-agonist effects of β-CNA and C-CAM were mediated by MOR. The assay conditions are identical to thos for Figure except the inverse antagonists are premixed with the neutral antagonists.

EXAMPLE 2

Effects of Antagonists on cAMP Levels of Intact HEK-MOR Cells

Selected opioid antagonists were also tested for their effects on cAMP levels in the absence of any agonist both in untreated and morphine-pretreated HEK-MOR cells. Opioid receptors couple to Gi/Go proteins and inhibit adenylate cyclase. Thus, inverse agonists should release tonic inhibition of adenylate cyclase by MOR and increase cAMP levels, whereas neutral antagonists have no effect.

HEK-MOR cells were cultured in 24 well plates for 3–4 days, labeled with 2 µCi/mL $^3$H-adenine for 2 hrs, and washed twice with 2 mL serum-free medium. Cells were then incubated with 100 µM forskolin in the presence or absence of drugs at 37° C. for 30 minutes at a concentration of 1 µM The reactions were terminated by adding 1 mL 5% trichloroacetic acid containing 1 mM ATP and 1 mM cAMP. $^3$H-cAMP was separated as described by Wong (Wong Y. H., Methods in Enzymology, 238, p 81–94 (1994)). Results were expressed as ratios of $^3$H-cAMP over total $^3$H-ATP, $^3$H-ADP and $^3$H-cAMP pools. For morphine pretreatment experiments, cells were incubated with 1 µM morphine for 16 hours before experiments, and then cells were labeled with 2 µCi/mL $^3$H-adenine for 2 hrs. 1 µM morphine was included in the $^3$H-adenine labeling medium.

Figure 2:
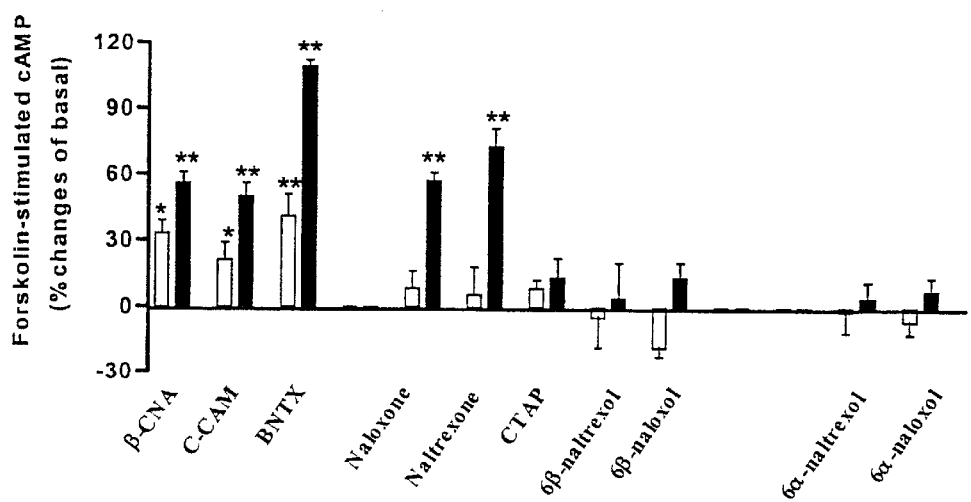
FIG. 2 is a graph showing the results of the indicated opioid antagonists on cAMP levels in intact HEK-MOR cells in order to determine which antagonists are neutral antagonists. The effects of inverse agonists are expected to be opposite to that observed in the $^{35}$S-GTPγS binding to HEK-MOR cell membranes (FIG. 1). Mean±SD, *, ** versus % changes of basal done with mock-transfected cells. P<0.05, P<0.01, respectively, n=6, ANOVA with Dunnett post test.
Figure 3:
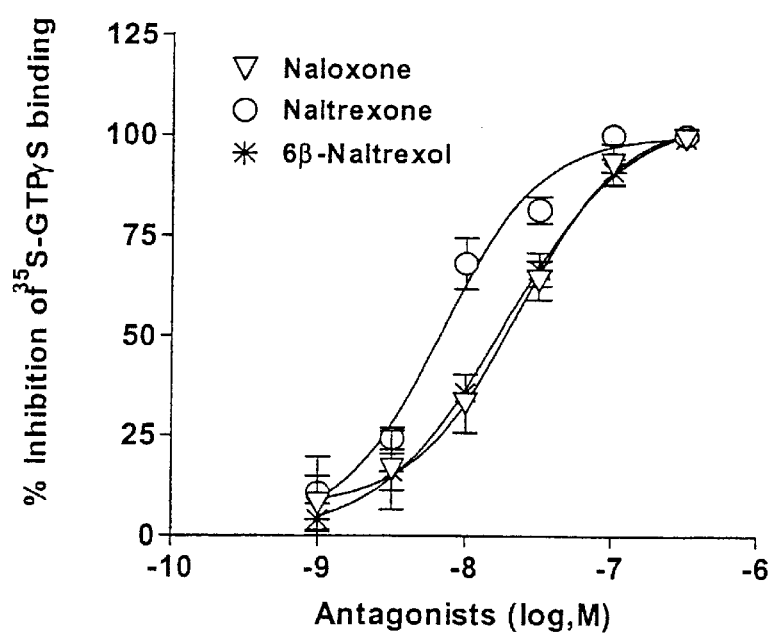
FIG. 3 is a graph of dose-response curves for naloxone, naltrexone and 6β-naltrexol for inhibiting 100 nM morphine-activated $^{35}$S-GTPγS binding in HEK-MOR cell membranes. Mean±SD, n=3.

As shown in FIG. 2 none of the test compounds had any effects on cAMP levels. These results are similar to the results of the $^{35}$S-GTPγS binding assay set forth above. Further, FIG. 2 also shows that the inverse agonists identified by $^{35}$S-GTPγS binding in cell membranes, β-CNA, C-CAM and BNTX, increased forskolin stimulated cAMP levels in both untreated and morphine-pretreated HEK-MOR cells. The effect was consistently greater in treated compared to untreated cells. Naloxone and naltrexone had no significant effect in untreated cells but increased forskolin stimulated cAMP levels in morphine-pretreated cells. The neutral antagonists, CTAP, 6β-naloxol, 6α-naloxol and 6β-naltrexol, 6α-naltrexol had no effect on forskolin-stimulated cAMP levels in both untreated and morphine-pretreated cells.

These results mirror the results obtained from $^{35}$S-GTPγS binding assay in HEK-MOR cell membranes using 1 mM $Mg^{2+}$ described above and depicted graphically in FIG. 1, with opposite effects of inverse agonists on cAMP levels and $^{35}$S-GTPγS binding activity as expected.

EXAMPLE 3

Binding of Antagonists to MOR and DOR

Binding potencies of naloxone and naltrexone were compared to those of the following naloxone and naltrexone analogs: 6β-naltrexol, 6β-naloxol, 6α-naltrexol, 6α-naloxol, and 6β-naltrexamine using equilibrium binding analysis with $^3$H-naloxone as the tracer. Again the results obtained for 6β-naltrexamide were similar to the results for 6β-naltrexamine. Specifically, cell membranes used for $^3$H-naloxone binding assay were prepared as described above for $^{35}$S-GTPγS binding assay. Membranes (20 µg protein) were incubated with 2 nM $^3$H-naloxone in the absence or presence of 1 µM concentration of the indicated drugs at 25° C. for 1 hr. Incubations were terminated by rapid filtration onto glass-fiber filters (Schleicher & Schuell, Keene, N.H.). The filters were washed with 10 mL ice-cold PBS and the radioactivity quantified using liquid scintillation counting. Each antagonist was tested in triplicate and the Ki values presented in the Table are the mean of the triplicate analysis±SD.

The Ki values were calculated as follows: $K_i=IC_{50}/(1+L/Kd)$ where L is the concentration of $^3$H-naloxone used in the binding experiments (2 nM). Kd for naloxone was 0.8 nM and 2 nM at MOR and DOR, respectively, as determined from the saturation binding curves of $^3$H-naloxone. The results show that each of the neutral antagonists, which are analogs of naloxone and naltrexone, had similar affinity for MOR. Moreover, each neutral antagonist also displayed potent DOR binding, with a 2–3 fold selectivity for MOR over DOR.

TABLE

| Compounds | $K_i$ value (nM) | |
|---|---|---|
| | µ opioid receptor | δ opioid receptor |
| Naloxone | 0.81 ± 0.20 | 1.80 ± 0.40 |
| Naltrexone | 0.30 ± 0.04 | 1.20 ± 0.09 |
| 6β-Naltrexol | 0.80 ± 0.21 | 2.10 ± 0.01 |
| 6β-Naloxol | 1.10 ± 0.02 | 2.30 ± 0.05 |
| 6β-Naltrexamine | 0.63 ± 0.05 | 2.30 ± 0.09 |
| 6α-Naltrexol | 0.53 ± 0.04 | 2.40 ± 0.10 |
| 6α-Naloxol | 0.63 ± 0.04 | 2.10 ± 0.20 |

EXAMPLE 4

Figure 4:
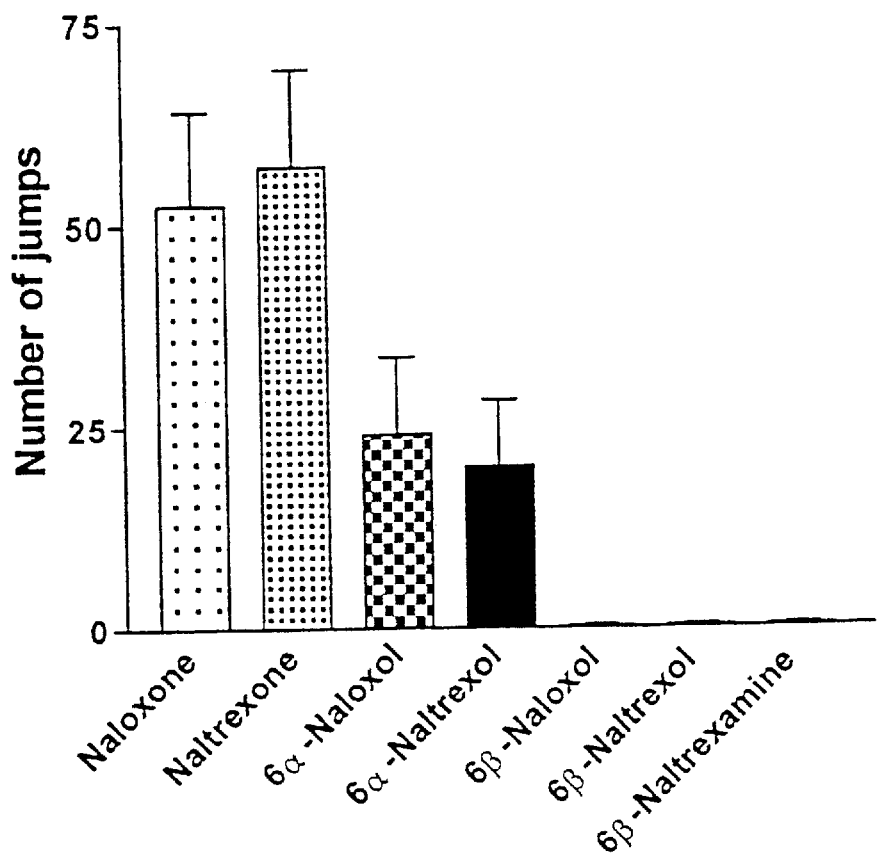
FIG. 4 is a graph showing the effects of antagonists (10 mg/kg i.p.) on withdrawal jumping in an acute mouse model of morphine dependence.

Antagonistic Effect of Naloxone, Naltrexone, and 6β-Naltrexol on Morphine-stimulated $^{35}$S-GTPγS BINDING in HEK-MOR Cell Membranes Morphine-stimulated $^{35}$S-GTPγS binding in HEK-MOR membranes was dose-dependently inhibited by the opioid antagonists naloxone, naltrexone and the neutral antagonist analog 6β-naltrexol (FIG. 4). While naltrexone was slightly more potent ($IC_{50}$=6.8±0.1 nM), 6βnaltrexol and naloxone were equally potent ($IC_{50}$=18±1 nM and 23±1 nM, respectively). This result is consistent with the result obtained from $^3$H-naloxone binding analysis (See the Table), indicating that receptor-binding and antagonistic potency of 6β-naltrexol fall in between those of naltrexone and naloxone.

In vivo Testing

Animal Subjects

Adult, male ICR mice (20–35 g, Harlan Industries, Cleveland, Ohio) were housed in groups of five in Plexiglas chambers with food and water available ad libitum. Animals were maintained in a temperature-controlled colony on a 12-hr light/dark cycle. All Studies were conducted in accordance with the Guide for the Care and Use of Laboratory Animals as adopted by the National Institute of Health.

Modes of Administration

Morphine sulfate was dissolved in distilled water for i.c.v. injections and physiological saline for i.p. injections. All antagonists were dissolved in physiological saline for i.p. injections immediately prior to use, and selected antagonists were also dissolved in distilled water for i.c.v. injections. Administration of morphine sulfate (and of selected antagonists) by the i.c.v. route of administration was accomplished by direct injection into the left lateral ventricle as previously described in Porreca F. et al., J. Pharmacol. Exp. Ther., 230, p 31–348 (1984).

Briefly, mice were lightly anesthetized with ether, and a small incision was made along the midline of the scalp. An injection was made using a 25 µL Hamilton syringe at a point 2 mm caudal and 2 mm lateral from bregma. The injection was made using a 27 gauge needle at a depth of 3 mm in a volume of 5 µL. Intraperitoneal injections (i.p.) were administered using a 1 mL syringe with a 30 gauge needle.

Physical Dependence Studies

Selected compounds were tested for their ability to elicit an opioid withdrawal syndrome in mice treated either acutely or chronically with morphine as described in Bilsky E. J. et al., *J. Pharmacol. Exp. Ther.*, 277, p 484–490 (1996). For the acute dependence, mice were pretreated with a single injection of morphine (100 mg/kg, s.c., −4 hr). Chronic morphine exposure consisted of implanting a 75 mg morphine pellet s.c. under ether anesthesia and waiting 72 hr.

EXAMPLE 5

Acute Dependcy Model

To assess precipitation of withdrawal, mice which had been pretreated once with morphine (100 mg/kg, s.c., −4 hr) were injected i.p. with 10 mg/kg doses of the following compounds: naloxone, naltrexone, 6α-naloxol, 6α-naltrexol, 6β-naltrexol, 6β-naloxol, 6β-naltrexamine and 6β-naltrexamide (results not present in FIG. 4). Immediately following administration of the selected antagonist, animals were placed in a clear Plexiglas cylinder and observed for 15 minutes. The number of vertical jumps was recorded during this time and served as a measure of withdrawal severity (Yano, I. and Takemori, A. E., *Res. Commun. Chem. Pathol. Pharmacol.*, 16, p 721–734 (1977)).

The results are depicted graphically in FIG. 4 and show that, as expected, naloxone and naltrexone precipitated robust withdrawal jumping. Both the 6α-naloxol and 6α-naltrexol analog showed approximately 50% less jumping that their parent compound. However, the 6β-naltrexol, 6β-naloxol, 6β-naltrexamine and 6β-naltrexamide elicited no withdrawal jumping.

EXAMPLE 6

Chronic Dependency Model

Figure 5:
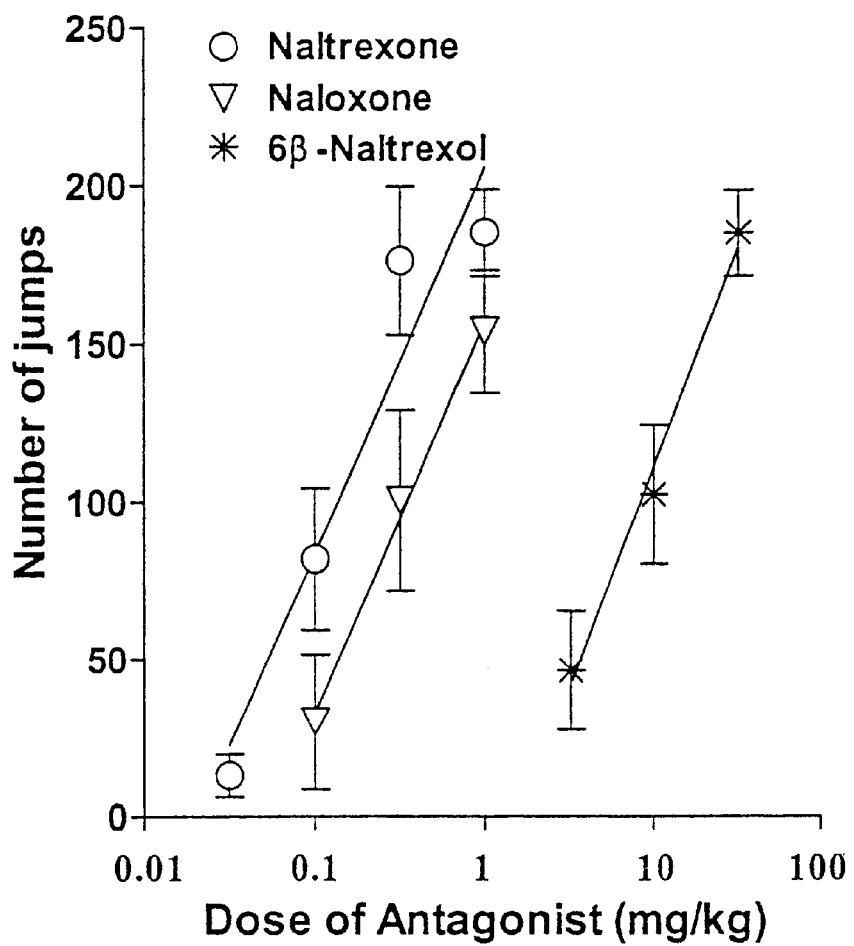
FIG. 5 is a graph of dose-response curves for naltrexone, naloxone, and 6β-naltrexol given i.p. for eliciting withdrawal jumping in a chronic mouse model of morphine dependence (morphine pellet implantation). Mean±SEM, n=10–15.

Increasing doses of naloxone (0.1, 0.5 and 1.0 mg/kg), naltrexone (0.05, 0.1, 0.5 and 1.0 mg/kg) and 6β-naltrexol (5, 10 and 100 mg/kg) were also tested for their ability to elicit withdrawal jumping in a chronic model of physical dependence, using morphine pellet implantation. The results are depicted graphically in FIG. 5. Naltrexone and naloxone (i.p.) potently produced dose-related increases in withdrawal jumping that appeared to plateau at approximately 200 jumps/mouse. The doses of naltrexone and naloxone needed to elicit 100 jumps/mouse were approximately 0.1 and 0.3 mg/kg, respectively. In contrast, 6β-naltrexol was much less potent at precipitating withdrawal jumping, with a calculated dose of 10 mg/kg needed to precipitate 100 jumps on average. This is consistent with the ability of 6β-naltrexol to diminish withdrawal (at a dose of 10 mg/kg) in the acute mouse model of morphine dependence, in which antagonists are generally less potent. Similarly, 6β-naltrexamide had low potency in eliciting withdrawal jumping with and $EC_{50}$ similar to 6β-naltrexol.

EXAMPLE 7

Antinociceptive Studies

Antinociception was assessed using the 55° C. warm-water tail flick assay. The latency to the first sign of a rapid tail-flick was used as the behavioral endpoint. Each mouse was tested for base-line latency by immersing its tail in the water bath and recording the time to response. Mice that displayed a tail-flick latency of greater than 5 seconds were eliminated from further testing. An i.p. injection of vehicle or one of the test compounds was followed 10 minutes later by morphine sulfate (20 nmol, i.c.v., $A_{90}$ dose producing antinociception) administration. Selected antagonists were also injected i.c.v. to assess relative access to the CNS from the i.p. route. Mice were tested for antinociception 30 min after morphine administration. To avoid tissue damage, a maximal score was assigned to mice not responding within 15 seconds. Percent antinociception was calculated as: (test latency−control latency)/(15−control latency)×100.

Figure 6:
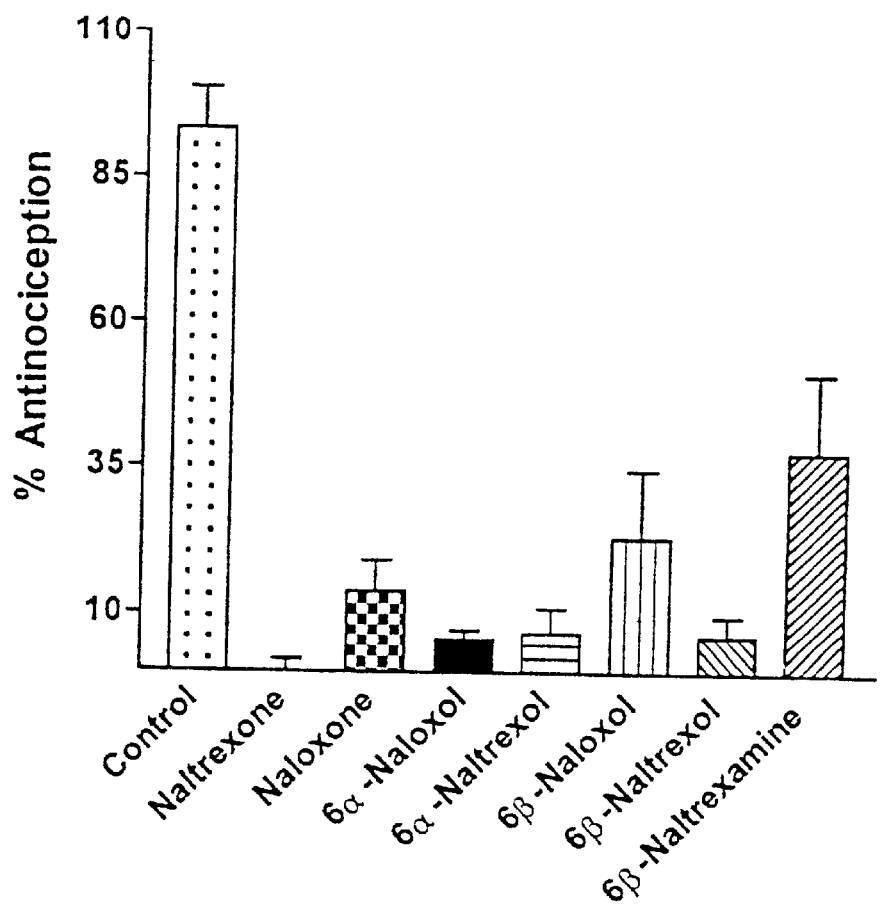
FIG. 6 is a graph showing the effect of antagonists (10 mg/kg i.p.) in suppressing morphine (20 nmole i.c.v.) induced antinociception (tail flick assay). Mean±SEM, n=10–15.

Specifically, naltrexone, naloxone, 6α-naloxol, 6α-naltrexol, 6β-naloxol, 6β-naltrexol and 6β-naltrexamine were administered i.p at a dose of 10 mg/kg to assess their ability to block the antinociceptive actions of an i.c.v. $A_{90}$ dose of morphine (20 nmol/injection) in the 55° C. tail-flick assay. The results are shown graphically in FIG. 6. 6β-naltrexamide was also tested and had an effect similar to 6β-naltrexamine. Therefore, these two compounds are less potent centrally than 6β-naltrexol, even though the demonstrated similar receptor binding potency. Hese comouonds-may be preferred for selectively blocking periperal opioid drug action, without the adverse side effects (e.g., diarrhea or constipation). The results show that the prototypal opioid antagonists naloxone and naltrexone blocked morphine antinociception. Further, the 6α-naloxol and 6α-naltrexol, as well as 6β-naltrexol, also blocked the antinociceptive actions of morphine. However, the 6β-naloxol and 6β-naltrexamine produced only partial blockade. Morphine was given i.c.v. to assure that the antagonist effects are centrally mediated.

Figure 7:
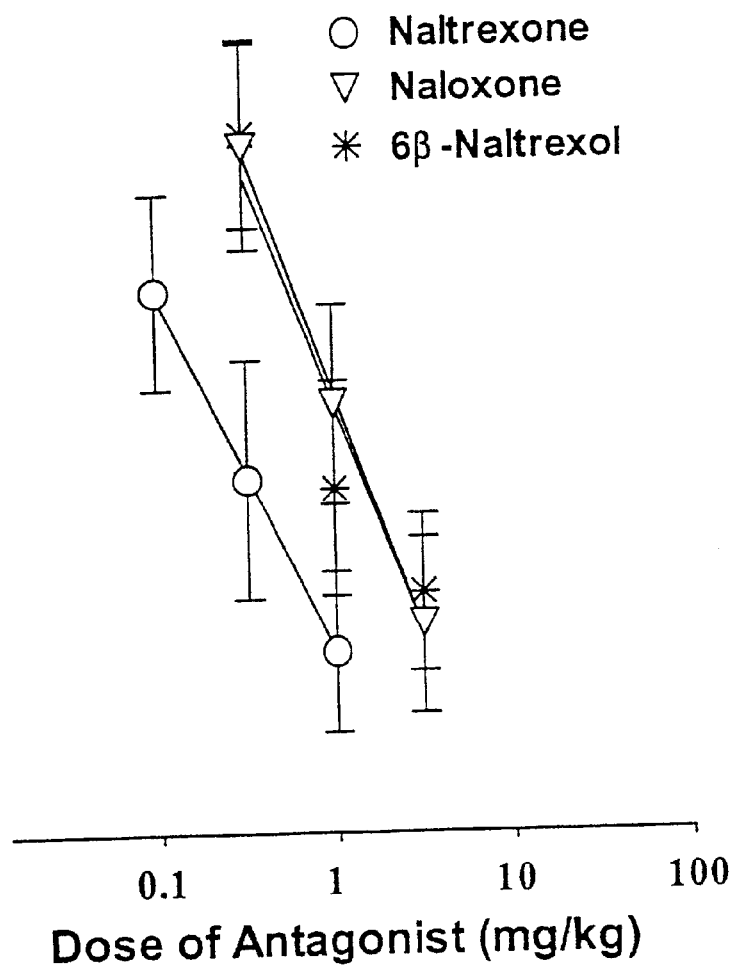
FIG. 7 is a dose-response curves for naltrexone, naloxone, and 6β-naltrexol given i.p. for antagonism of morphine (20 nmole i.c.v.). Mean±SEM, n=10–15.

In addition, complete i.p. antagonist dose-response curves were developed to determine the rank order for naltrexone, naloxone and the neutral antagonist 6β-naltrexol against morphine-induced antinociception (20 nmol morphine; $A_{90}$ dose, i.c.v.). The results are depicted graphically in FIG. 7. Morphine was administered i.c.v to assure that the test compound acted centrally. The rank order of potency was naltrexone, 6β-naltrexol and naloxone ($ID_{50}$ value [95% C.I.]: 0.22 mg/kg [0.11–0.43]; 1.0 mg/kg [0.58–1.7]; 1.1 mg/kg [0.66–1.8], respectively).

A second dose-response curve was also generated, as described above, but wherein the antagonists were administered using an i.c.v. injection. The rank order of potency ($ID_{50}$ value [95% C.I.]) remained similar for naltrexone, 6β-naltrexol and naloxone: 0.26 nmol [0.15–0.46], 2.3 nmol [1.3–4.0], and 3.4 nmol [1.7–6.8], respectively.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for the treatment of drug-dependency in an individual in need thereof comprising administering to the individual a therapeutically effective amount of a naloxone analog or naltrexone analog or a pharmaceutically acceptable salt thereof which is a neutral antagonist at the $\mu$ opioid receptor.

2. The method of claim 1, wherein the naltrexone analog is represented by Formula I:

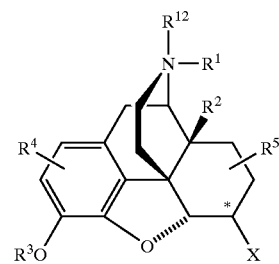

wherein:

R¹ is cycloalkyl(alkyl) or cycloalkenyl(alkyl);
² is H, OH or esters thereof;
³ is H, alkyl or (alkyl) C=O;
⁴ and ⁵ are independently H, halogen, alkyl, alkoxy, nitro, amino, cyano, carboxyl or acyl which can be substituted for one or more hydrogens on the ring;
X is —OR⁶, —NR⁷R⁸R⁹,—NCOR¹⁰, —NO₂, —SR¹¹;

wherein,

P⁶ and R¹¹ are independently selected from H, alkyl, substituted alkyl; cycloalkyl, substituted cycloalkyl, aryl, substituted aryl, acyl, or aroyl;
⁷, R⁸ and R¹⁰ are independently selected from hydrogen, alkyl, substituted alkyl, cycloalkyl, substituted cycloalkyl, aryl, or substituted aryl;
P⁹ and R¹² can be present or absent and are independently selected from hydrogen, alkyl, substituted alkyl, cycloalkyl, substituted cycloalkyl, aryl, or substituted aryl or pharmaceutically acceptable salts thereof.

3. The method of claim 2, wherein the naltrexone analog is

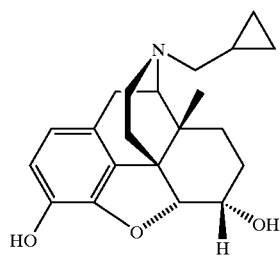

6α-Naltrexol

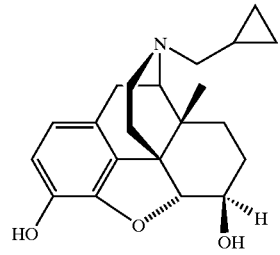

6β-Naltrexol

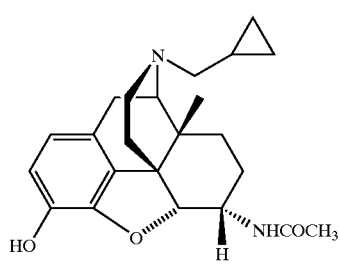

6α-Naltrexamide

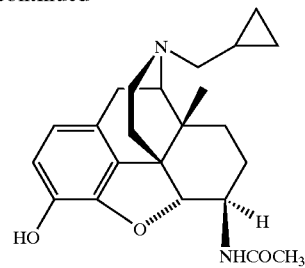

6β-Naltrexamide

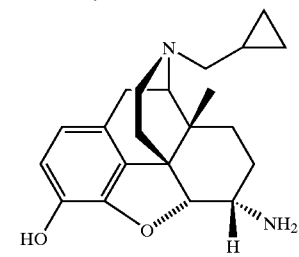

6α-Naltrexamine

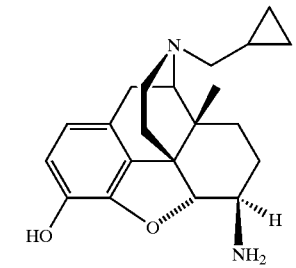

6β-Naltrexamine or the pharmaceutically acceptable salts thereof.

4. The method of claim 1, wherein the naloxone analog is represented by Formula I:

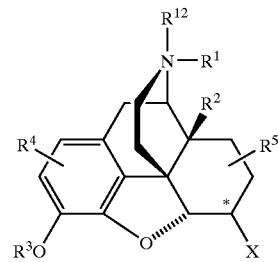

wherein:
R¹ is alkenyl;
R² is H, OH or esters thereof;
R³ is H, alkyl or (alkyl)C=O;
R⁴ and R⁵ are independently H, halogen, alkyl, alkoxy, nitro, amino, cyano, carboxyl or acyl which can be substituted for one or more hydrogens on the ring;
X is —OR⁶, —NR⁷R⁸R⁹, —NCOR¹⁰, —NO₂, -SR¹¹;
wherein,
R⁶ and R¹¹ are independently selected from H, alkyl, substituted alkyl, cycloalkyl, substituted cycloalkyl, aryl, substituted aryl, acyl, or aroyl, R⁷, R⁸ and R¹⁰ are independently selected from hydrogen, alkyl, substituted alkyl, cycloalkyl, substituted cycloalkyl, aryl, or substituted aryl;

R[9] and R[12] can be present or absent and are independently selected from hydrogen, alkyl, substituted alkyl, cycloalkyl, substituted cycloalkyl, aryl, or substituted aryl or pharmaceutically acceptable salts thereof.

5. The method of claim 4, wherein the naloxone analog is

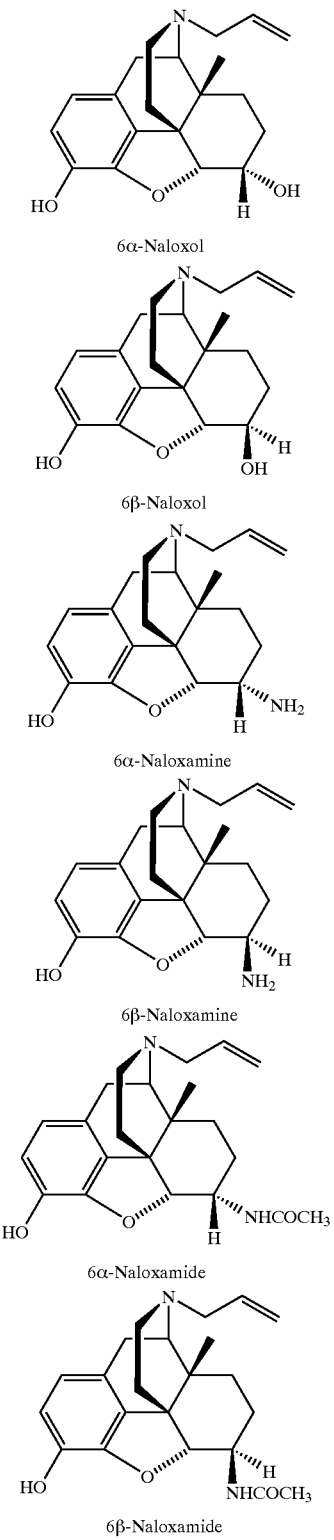

or pharmaceutically acceptable salts thereof.

6. The method of claim 1, wherein the individual is in long-term therapy to prevent relapse to drug dependency.

7. The method of claim 1, wherein the individual is undergoing drug overdose treatment.

8. The method of claim 1, wherein the individual is undergoing active withdrawal treatment.

9. A method for the treatment of drug-dependency in an individual in need thereof comprising administering to the individual a therapeutically effect amount of a sustained release composition comprising:

a. biocompatible polymer; and b. an effective amount of a neutral antagonist selected from a naloxone analog or naltrexone analog or the pharmaceutically acceptable salts thereof which are neutral antagonist at the $\mu$ opioid receptor.

10. The method of claim 9, wherein the naltrexone analog is represented by Formula I:

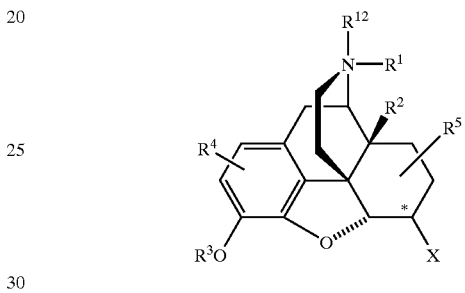

wherein:

$R^1$ is cycloalkyl(alkyl) or cycloalkenyl(alkyl);

$R^2$ is H, OH or esters thereof;

$R^3$ is H, alkyl or (alkyl)C=O;

$R^4$ and $R^5$ are independently H, halogen, alkyl, alkoxy, nitro, amino, cyano, carboxyl or acyl which can be substituted for any hydrogen on the ring; X is —OR$^6$, —NR$^7$R$^8$R$^9$, —NCOR$^{10}$, —NO$_2$, —SR$^{11}$;

wherein,

R[6] and R[11] are independently selected from H, alkyl, substituted alkyl, cycloalkyl, substituted cycloalkyl, aryl, substituted aryl, acyl, or aroyl, R[7,] R[8] and R[10] are independently selected from hydrogen alkyl, substituted alkyl, cycloalkyl, substituted cycloalkyl, aryl, or substituted aryl, R[9] and R[12] can be absent or present and are independently selected from hydrogen alkyl, substituted alkyl, cycloalkyl, substituted cycloalkyl, aryl, or substituted aryl, or pharmaceutically acceptable salts thereof.

11. The method of claim 10, wherein the naltrexone analog is

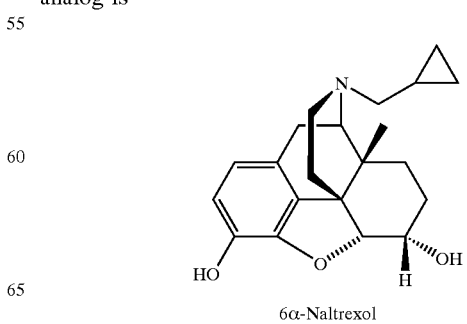

-continued

6β-Naltrexol

6α-Naltrexamide

6β-Naltrexamide

6α-Naltrexamine

6β-Naltrexamine or the pharmaceutically acceptable salts thereof.

12. The method of claim 9, wherein the naloxone analog is represented by Formula I:

wherein:
R$^1$ is alkenyl;
R$^2$ is H, OH or esters thereof;
R$^3$ is H, alkyl or (alkyl)C=O;
R$^4$ and R$^5$ are independently H, halogen, alkyl, alkoxy, nitro, amino, cyano, carboxyl or acyl which can be substituted for one or more hydrogens on the ring; X is —OR$^6$, —NR$^7$R$^8$R$^9$, —NCOR$^{10}$, —NO$_2$, —SR$^{11}$;
wherein,
R$^6$ and R$^{11}$ are independently selected from H, alkyl, substituted alkyl, cycloalkyl, substituted cycloalkyl, aryl, substituted aryl, acyl, or aroyl, R$^7$, R$^8$ and R$^{10}$ are independently selected from hydrogen, alkyl, substituted alkyl, cycloalkyl, substituted cycloalkyl, aryl, or substituted aryl,
R$^9$ and R$^{12}$ can be absent or present and are independently selected from hydrogen, alkyl, substituted alkyl, cycloalkyl, substituted cycloalkyl, aryl, or substituted aryl or pharmaceutically acceptable salts thereof.

13. The method of claim 12, wherein the naloxone analog is

6α-Naloxol

6β-Naloxol

6α-Naloxamine

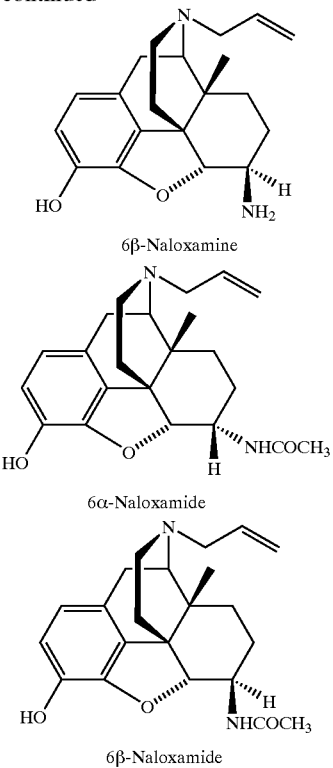

6β-Naloxamine

6α-Naloxamide

6β-Naloxamide or pharmaceutically acceptable salts thereof.

14. The method of claim 9, wherein the individual is in long-term therapy to prevent relapse to drug dependency.

15. The method of claim 9, wherein the individual is undergoing drug overdose treatment.

16. The method of claim 9, wherein the individual is undergoing active withdrawal treatment.

17. A method for the precipitation of withdrawal from acute opioid effects in an individual in need thereof comprising administering to the individual a therapeutically effective amount of a naloxone analog or naltrexone analog or a pharmaceutically acceptable salt thereof which is a neutral antagonist at the μ opioid receptor.

18. The method of claim 1, wherein the compounds act in one or more of centrally or peripherally when administered in one or more of peripherally or centrally.

19. The method of claim 9, wherein the sustained release composition releases a therapeutically effective amount of the neutral antagonist for about 1 day.

20. The method of claim 9, wherein the sustained release composition releases a therapeutically effective amount of the neutral antagonist for greater than about 2 days.

21. The method of claim 19, the sustained release composition releases a therapeutically effective amount of the neutral antagonist for about 7 days.

22. The method of claim 17 wherein the individual is a human.

23. The method of claim 17 wherein the individual is a mammal or non-mammal animal.

24. The method of claim 23 wherein said individual is one or more of the group consisting of canine, murine, feline, bovine, ovine, swine or caprine.

25. A method of alleviating adverse effects associated with opioid use by an individual in need thereof comprising administration to the individual of a therapeutically effective amount of a naloxone analog or naltrexone analog or a pharmaceutically acceptable salt thereof which is a neutral antagonist at the μ opioid receptor.

26. The method of claim 25 wherein an individual is using opioids for analgesia.

27. The method of claim 25 wherein an individual is experiencing opioid withdrawal effects.

28. The method of claim 25 wherein the adverse effects of opioid use include respiratory depression.

29. The method of claim 25 wherein the adverse effects of opioid use include alteration of gastrointestinal transit.

* * * * *

UNITED STATES PATENT AND TRADEMARK OFFICE
CERTIFICATE OF CORRECTION

PATENT NO.    : 6,713,488 B2
DATED         : March 30, 2004
INVENTOR(S)   : Wolfgang Sadee and Danxin Wang It is certified that error appears in the above-identified patent and that said Letters Patent is hereby corrected as shown below:

Column 26,
Line 53, cancel the text beginning with "2. The method of claim 1" to and ending with "aryl or pharmaceutical acceptable salts thereof."

Column 27,
Line 27, and insert the following claim:

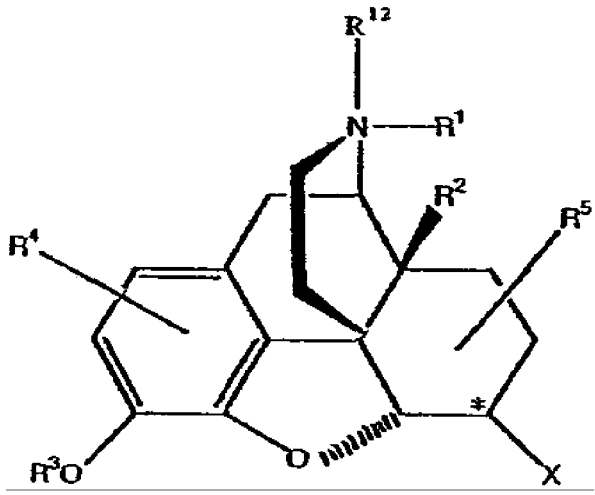

2. The method of Claim 1, wherein the naltrexone analog is represented by Formula I:
wherein:
  $R^1$ is cycloalkyl(alkyl) or cycloalkenyl (alkyl);
  $R^2$ is H, OH or esters thereof;
  $R^3$ is H, alkyl or (alkyl) C=O;
  $R^4$ and $R^5$ are independently H, halogen, alkyl, alkoxy, nitro, amino, cyano, carboxyl or acyl which can be substituted for one or more hydrogens on the ring;
  X is $-OR^6$, $-NR^7R^8R^9$, $-NCOR^{10}$, $-NO_z$, $-SR^{11}$;
wherein,

UNITED STATES PATENT AND TRADEMARK OFFICE
CERTIFICATE OF CORRECTION

PATENT NO. : 6,713,488 B2
DATED : March 30, 2004
INVENTOR(S) : Wolfgang Sadee and Danxin Wang It is certified that error appears in the above-identified patent and that said Letters Patent is hereby corrected as shown below:

Column 27, (cont.)
$R^6$ and $R^{11}$ are independently selected from H, alkyl, substituted alkyl; cycloalkyl, substituted cycloalkyl, aryl, substituted aryl, acyl, or aroyl;
$R^7$, $R^8$ and $R^{10}$ are independently selected from hydrogen, alkyl, substituted alkyl, cycloalkyl, substituted cycloalkyl, aryl, or substituted aryl;
$R^9$ and $R^{12}$ can be present or absent and are independently selected from hydrogen, alkyl, substituted alkyl, cycloalkyl, substituted cycloalkyl, aryl, or substituted aryl
or pharmaceutically acceptable salts thereof.

Signed and Sealed this

Twenty-fifth Day of January, 2005

JON W. DUDAS
*Director of the United States Patent and Trademark Office*